(12) United States Patent
Chen et al.

(10) Patent No.: US 12,629,527 B2
(45) Date of Patent: May 19, 2026

(54) IMPLANTABLE MEDICAL DEVICE WITHOUT A WIRE-WOUND COIL CONFIGURED TO RECEIVE WIRELESS POWER FROM AN EXTERNAL CHARGER

(71) Applicant: Boston Scientific Neuromodulation Corporation, Valencia, CA (US)

(72) Inventors: Joey Chen, Stevenson Ranch, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1079 days.

(21) Appl. No.: 17/596,018

(22) PCT Filed: Jun. 8, 2020

(86) PCT No.: PCT/US2020/036668
§ 371 (c)(1),
(2) Date: Dec. 1, 2021

(87) PCT Pub. No.: WO2020/251900
PCT Pub. Date: Dec. 17, 2020

(65) Prior Publication Data
US 2022/0323771 A1 Oct. 13, 2022

Related U.S. Application Data

(60) Provisional application No. 62/861,778, filed on Jun. 14, 2019.

(51) Int. Cl.
*A61N 1/372* (2006.01)
*A61N 1/375* (2006.01)
(Continued)

(52) U.S. Cl.
CPC ......... *A61N 1/372* (2013.01); *A61N 1/37229* (2013.01); *A61N 1/3754* (2013.01);
(Continued)

(58) Field of Classification Search
CPC . A61N 1/37229; A61N 1/3754; A61N 1/3787
See application file for complete search history.

(56) References Cited

U.S. PATENT DOCUMENTS 5,906,634 A * 5/1999 Flynn .................. A61N 1/3752
607/37
6,181,969 B1 1/2001 Gord
(Continued)

FOREIGN PATENT DOCUMENTS

CN 106924878 A 7/2017

OTHER PUBLICATIONS

International Search Report and Written Opinion regarding corresponding PCT Application No. PCT/US2020/036668, mailed Oct. 5, 2020.
(Continued)

*Primary Examiner* — Unsu Jung
*Assistant Examiner* — Laura Hodge
(74) *Attorney, Agent, or Firm* — Lewis & Reese, PLLC

(57) ABSTRACT

Implantable medical devices (IMDs) are disclosed which are capable of wirelessly receiving power from a magnetic field to power the IMD or charge its battery, but which do not use a wire-wound coil for magnetic field reception. The IMD can include a case housing control circuitry for the IMD, in which at least a portion of the case is conductive, with a case current formed in the conductive case portion in response to the magnetic field. The IMD includes power reception circuitry inside the case, and includes various examples of first and second electrical connections used to divert at least some of the case current as a power current to the power reception circuitry, thus allowing the power reception circuitry to use the power current to provide power to the IMD or to charge its battery.

16 Claims, 11 Drawing Sheets

(51) Int. Cl.
    *A61N 1/378*         (2006.01)
    *H01G 4/35*         (2006.01)
    *H01Q 1/22*         (2006.01)

(52) U.S. Cl.
    CPC ............. *A61N 1/3787* (2013.01); *H01G 4/35*
              (2013.01); *H01Q 1/22* (2013.01)

(56) References Cited

U.S. PATENT DOCUMENTS

| | | | |
|---|---|---|---|
| 6,516,227 | B1 | 2/2003 | Meadows et al. |
| 7,177,698 | B2 | 2/2007 | Klosterman et al. |
| 7,289,853 | B1 | 10/2007 | Campbell et al. |
| 7,295,878 | B1 | 11/2007 | Meadows et al. |
| 7,818,068 | B2 | 10/2010 | Meadows et al. |
| 7,979,126 | B2 | 7/2011 | Payne et al. |
| 8,010,205 | B2 | 8/2011 | Rahman et al. |
| 8,081,925 | B2 | 12/2011 | Parramon et al. |
| 8,214,042 | B2 | 7/2012 | Ozawa et al. |
| 8,457,756 | B2 | 6/2013 | Rahman |
| 8,577,474 | B2 | 11/2013 | Rahman et al. |
| 8,606,362 | B2 | 12/2013 | He et al. |
| 8,620,436 | B2 | 12/2013 | Parramon et al. |
| 8,626,297 | B2 | 1/2014 | Jaax et al. |
| 8,630,705 | B2 | 1/2014 | Mann et al. |
| 8,666,491 | B2 | 3/2014 | Chen et al. |
| 8,738,138 | B2 | 5/2014 | Funderburk et al. |
| 9,026,211 | B2 | 5/2015 | Yan et al. |
| 9,067,072 | B2 | 6/2015 | Tahmasian et al. |
| 9,393,433 | B2 | 7/2016 | Parramon et al. |
| 9,867,994 | B2 | 1/2018 | Parramon et al. |
| 2004/0215280 | A1* | 10/2004 | Dublin ............... A61N 1/37229 |
| | | | 607/36 |
| 2006/0247712 | A1 | 11/2006 | Fuller et al. |
| 2008/0039898 | A1* | 2/2008 | Lim ......................... H01Q 1/22 |
| | | | 607/32 |
| 2009/0240309 | A1* | 9/2009 | Rahman .................. H01Q 9/42 |
| | | | 343/702 |
| 2010/0161002 | A1 | 6/2010 | Aghassian et al. |
| 2011/0112612 | A1 | 5/2011 | Rahman |
| 2014/0163645 | A1* | 6/2014 | Dinsmoor ............ A61N 1/3787 |
| | | | 607/60 |
| 2015/0066113 | A1 | 3/2015 | Van Funderburk |
| 2015/0080982 | A1 | 3/2015 | Van Funderburk |
| 2015/0174415 | A1* | 6/2015 | Angara ................... H02J 50/12 |
| | | | 320/108 |
| 2016/0359222 | A1* | 12/2016 | Li ............................. H01Q 1/36 |
| 2017/0151438 | A1 | 6/2017 | Orinski |
| 2017/0151440 | A1 | 6/2017 | Parramon et al. |
| 2017/0281936 | A1 | 10/2017 | Aghassian et al. |
| 2017/0361113 | A1 | 12/2017 | Aghassian et al. |
| 2018/0026470 | A1 | 1/2018 | Aghassian |
| 2018/0071520 | A1 | 3/2018 | Weerakoon et al. |
| 2018/0071522 | A1 | 3/2018 | Feldman et al. |
| 2018/0200527 | A1 | 7/2018 | Aghassian et al. |
| 2018/0212451 | A1* | 7/2018 | Schmidt .................. H02J 50/80 |
| 2019/0070421 | A1 | 3/2019 | Chen |
| 2019/0083796 | A1 | 3/2019 | Weerakoon et al. |
| 2019/0232066 | A1* | 8/2019 | Lim ..................... A61N 1/3754 |

OTHER PUBLICATIONS

Kod, Muayad, et al., "Feasibility Study of Using the Housing Cases of Implantable Devices as Antennas," IEEE, vol. 4, Sep. 29, 2016, pp. 6939-6949.
First Office Action regarding corresponding Chinese Patent Application No. 202080043882.3, mailed Jun. 19, 2024.

* cited by examiner

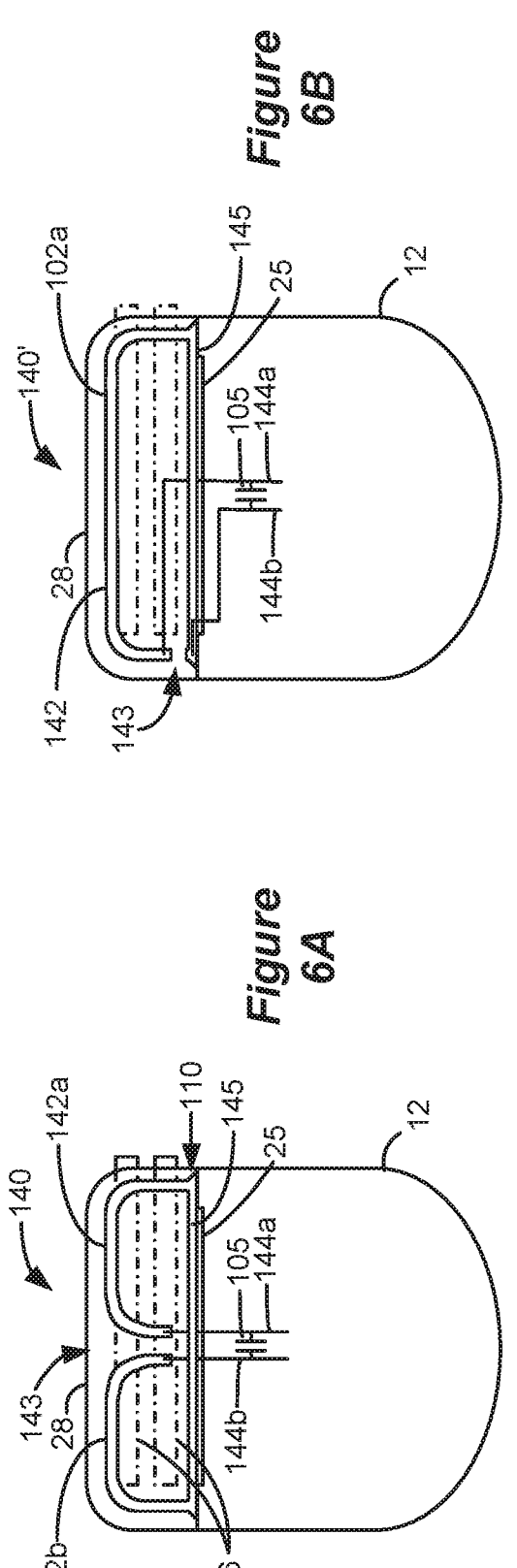
*Figure 6A*
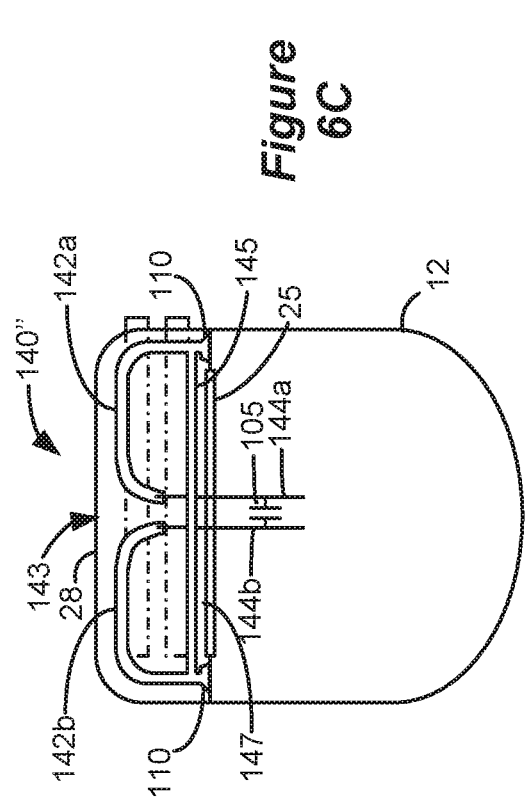
*Figure 6B*
*Figure 6C*

IMPLANTABLE MEDICAL DEVICE WITHOUT A WIRE-WOUND COIL CONFIGURED TO RECEIVE WIRELESS POWER FROM AN EXTERNAL CHARGER

FIELD OF THE INVENTION

The present invention relates to implantable medical devices and means for wireless receipt of power from an external charger.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1B, a SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the control circuitry 86 (FIG. 3) and battery 14 (FIG. 1B) necessary for the IMD 10 to function. The IMD 10 is coupled to electrodes Ex 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18, although the number of leads and electrodes is application specific and therefore can vary. The leads 18 couple to lead connectors 26 in the IMD 10, which are fixed in a non-conductive header material 28 such as an epoxy. Feedthrough pins 23 connect to electrode contacts (not shown) in the lead connectors 26, which pins pass through a hermetic feedthrough 25 on the top of the case 12, where they are connected to stimulation circuitry inside of the IMD 10's case. Control circuitry 86 can include stimulation circuitry configured to provide stimulation current to selected ones of the electrodes, and can comprise circuitry disclosed for example in U.S. Pat. Nos. 6,181,969, 8,606,362, 8,620,436, U.S. Patent Application Publications 2018/0071520 and 2019/0083796. The conductive case 12 material can also operate as a case electrode Ec to provide a return current path for currents provided at the lead based electrodes, Ex.

As shown in the cross-section of FIG. 1B, the IMD 10 typically includes a printed circuit board (PCB) 29, along with various electronic components 32 mounted to the PCB 29, some of which are discussed subsequently. The IMD 10 traditionally includes a charging coil 30 for charging or recharging the IMD's battery 14 using an external charger. The case 12 is typically formed of two clam-shell-like portions 12$i$ and 12$o$ that that are designed when implanted to respectively face the inside and outside of the patient.

These portions 12$i$ and 12$o$ are typically welded (11) together along the outer periphery of the case, and include flanges that are welded to the feedthrough 25. When so formed, the case 12 includes planar parallel major surfaces formed in the outside and inside case portions 12$o$ and 12$i$, and a generally planar top surface 12$t$ perpendicular to the major surfaces which includes the feedthrough 25.

FIGS. 2A and 2B show the IMD 10 in communication with external chargers, and two different examples of chargers 40 and 60 are shown. Both types of chargers 40 and 60 are used to wirelessly convey power in the form of an electromagnetic field 55 (referred to as a "magnetic field" for short) to the IMD 10, which power can be used to recharge the IMD's battery 14. The transfer of power from external charger 40 is enabled by a primary charging coil 44 in FIG. 2A, and by a primary charging coil 66 in FIG. 2B. FIG. 2A shows an example in which the charging coil 44 is integrated in the same housing as other charger electronics, while in FIG. 2B the charging coil 66 and charger electronics are separated into different housings and connected by a cable 68.

In FIG. 2A, the integrated charger 40 includes a PCB 46 on which electronic components 48 are placed, some of which are discussed subsequently. Charging coil 44 may be mounted to the PCB 46, and preferably on the side of the PCB that faces the IMD 10 as shown. A user interface, including touchable buttons, LEDs (not shown) and perhaps a display and a speaker (not shown), allows a patient or clinician to operate the external charger 40. In FIG. 2A, the user interface is shown simply as including an on/off button 42 used to turn the magnetic field 55 on or off. A battery 50 provides power for the external charger 40, which battery 50 may itself be rechargeable. Charger 40 is typically configured to be hand-holdable and portable, and is described further in U.S. Patent Application Publication 2017/0361113.

In FIG. 2B, the charger 60 comprises a charging coil assembly 62 and an electronics module 64 in separate housings which are connected by a cable 68. The charging coil assembly 62 includes the charging coil 66, while the electronics and user interface elements are provided by the electronics module 64. The electronics housing 64 may include a PCB 70, a battery 72, various control circuitry 74, and user interface elements 76 such as those mentioned above. Charger 60 despite generally being in two pieces 62 and 64 is also typically configured to be hand-holdable and portable, and is again described further in the above-referenced 2017/0361113 publication.

Transmission of the magnetic field 55 from either of chargers 40 or 60 to the IMD 10 occurs wirelessly and transcutaneously through a patient's tissue via inductive coupling. FIG. 3 shows details of the circuitry used to implement such functionality. Primary charging coil 44 or 66 in the external charger is energized via charging circuit 64 with an AC current, Icharge, to create the AC magnetic charging field 55. A tuning capacitor 45 is provided to form a resonant LC tank with the charging coil 44 or 66, which generally sets the frequency of the AC magnetic field 55.

The magnetic portion of the electromagnetic field 55 induces a current Icoil in the secondary charging coil 30 within the IMD 10, which current is received at power reception circuitry 81. Power reception circuitry 81 can include a tuning capacitor 80, which is used to tune the resonance of the LC circuit in the IMD to the frequency of the magnetic field. One skilled will understand that the capacitors 45 or 80 may be placed in series or in parallel with their respective coils (inductances) 44/66 or 30, although it is preferred that the capacitor 45 be placed in series with the coil 44/66 in the charger 40/60, while the capacitor 80 is placed in parallel with the coil 30 in the IMD 10. The power reception circuitry 81 further includes a rectifier 82 used to convert AC voltage across the coil 30 to DC a DC voltage Vdc. Power reception circuitry 81 may further include other conditioning circuitry such as charging and protection circuitry 84 to generate a Voltage Vbat which can be used to provide regulated power to the IMD 10, and to generate a current Ibat which is used to charge the battery 14. The frequency of the magnetic field 55 can be perhaps 80 kHz or so.

The IMD 10 can also communicate data back to the external charger 40 or 60, and this can occur in different manners. As explained in the above-referenced 2017/0361113 publication, the IMD 10 may employ reflected impedance modulation to transmit data to the charger, which is sometimes known in the art as Load Shift Keying (LSK), and which involves modulating the impedance of the charging coil 30 with data bits provided by the IMD 10's control circuitry 86. The IMD may also use a communications channel separate from that used to provide power to transmit data to the charger, although such alternative channel and the antenna required are not shown for simplicity. The charger 40 or 60 can include demodulation circuitry 68 to recover the transmitted data, and to send such data to the charger's control circuitry 72. Such data as telemetered from to the charger 40/60 from the IMD 10 can include information useful for the charger to know during charging, such as the IMD's temperature (as sensed by temperature sensor 87), the voltage Vbat of the IMD's battery 14, or the charging current Ibat provided to the battery. Charger 40/60 can use such telemetered data to control production of the magnetic field 55, such as by increasing or decreasing the magnitude of the magnetic field 55 (by increasing or decreasing Icharge), or by starting or stopping generation of the magnetic field 55 altogether. As explained in the above-referenced 2017/0361113 publication, the charger 40/60 may also be used to determine the alignment of the charging coil 44/66 to the IMD 10, and may include alignment indicators (LEDs or sounds) that a user can review to determine how to reposition the charger to be in better alignment with the IMD 10 for more efficient power transfer.

SUMMARY

An implantable medical device (IMD) configured to wirelessly receive power from an electromagnetic field is disclosed, which may comprising: a case housing control circuitry for the IMD, wherein at least a portion of the case is conductive, and wherein a case current is formed in the conductive case portion in response to the electromagnetic field; power reception circuitry inside the case; and first and second electrical connections to divert at least some of the case current as a power current to the power reception circuitry, wherein the power reception circuitry is configured to use the power current to provide power to the IMD.

In one example, the IMD further comprises a non-conductive header affixed to the case. In one example, at least one of the first and second electrical connections comprises an antenna portion in or on the header, resulting in at least one antenna portion in or on the header. In one example, the IMD further comprises one or more lead connectors in the header, a feedthrough between the header and the case, and a plurality of electrode feedthrough wires, wherein the electrode feedthrough wires connect to contacts in the lead connectors and pass through the feedthrough inside the case.

In one example, at least one of the first and second electrical connections comprises a feedthrough wire connected to the at least one antenna portion that passes through the feedthrough. In one example, the at least one antenna portion is formed of a material of the case. In one example, the case comprises a planar surface configured to face an outside of a patient when implanted, wherein the at least one antenna portion is offset in or on the header towards the outside planar surface. In one example, there is a first antenna portion in or on the header comprising the first electrical connection, and a second antenna portion in or on the header comprising the second electrical connection. In one example, the first antenna portion comprises a first end and a second end, and wherein the second antenna portion comprises a first end and a second end. In one example, the first electrical connection further comprises a first wire connected to the first end of the first antenna portion, wherein the second end of the first antenna portion is connected to the conductive case portion, wherein the second electrical connection further comprises a second wire connected to the first end of the second antenna portion, wherein the second end of the second antenna portion is connected to the conductive case portion. In one example, there is a single antenna portion in or on header comprising the first electrical connection. In one example, the single antenna portion comprises a first end and a second end, wherein the first electrical connection further comprises a first wire connected to the first end of the single antenna portion, wherein the second end of the single antenna portion is connected to the conductive case portion. In one example, the second electrical connection comprises a second wire connected to the conductive case portion. In one example, there is a single antenna portion in or on the header comprising the first electrical connection and second electrical connection. In one example, the single antenna portion comprises a cross member connected to the conductive case portion along its length. In one example, the first electrical connection comprises a first wire connected to a first end of the single antenna portion, and wherein the second electrical connection a second wire connected to a second end of the single antenna portion. In one example, the single antenna portion comprises a cross member connected to the conductive case portion at first contact and at a second contact, wherein there is a space between the cross member and the case between the first and second contacts. In one example, the first electrical connection comprises the first contact and a first wire connected to a first end of the single antenna portion, and wherein the second electrical connection comprises the second contact and a second wire connected to a second end of the single antenna portion. In one example, the first and second connections are not formed in or on the header. In one example, at least one of the first and second electrical connections comprises a wire connected to the conductive case portion. In one example, the first electrical connection comprises a first wire connected to the conductive case portion at a first contact, and wherein the second electrical connection comprises a second wire connected to the conductive case portion at a second contact. In one example, the first and second electrical connections are separated by a portion of the case having a first conductivity, and wherein the conductive case portion in which the case current is formed has a second conductivity higher than the first conductivity. In one example, the power reception circuitry comprises a rectifier configured to convert the power current to a DC voltage that is used to provide power to the IMD. In one example, the IMD further comprises a battery within the case, wherein the power reception circuitry is configured to use the power current to provide power to the IMD to charge the battery. In one example, the conductive case portion comprises a conductive layer applied to the case. In one example, the IMD does not include a header. In one example, the case comprises a dielectric material, and wherein the conductive case portion comprises a conductive window. In one example, the dielectric material comprises a ceramic. In one example, conductive window is affixed to the dielectric material in a manner to cover a hole in the dielectric material. In one example, the conductive window comprises a plate affixed on or in the dielectric material. In one example, the control circuitry further comprises stimulation circuitry to form stimulation currents at selected ones of a plurality of electrodes in contact with a patient's tissue, wherein the conductive window comprises one of the plurality of electrodes. In one example, the conductive window is configured to be in contact with a patient's tissue, and is further configured to operate as a case electrode. In one example, the power reception circuitry is not coupled to a wire-wound coil configured to receive the electromagnetic field.

An implantable medical device (IMD) configured to wirelessly receive power from an electromagnetic field is disclosed, which may comprise: a case housing control circuitry for the IMD, wherein at least a portion of the case is conductive, and wherein a case current is formed in the conductive case portion in response to the electromagnetic field; power reception circuitry inside the case; a nonconductive header affixed to the case; and first and second electrical connections to divert at least some of the case current as a power current to the power reception circuitry, wherein the first electrical connection comprises a first antenna portion in or on the header and wherein the second electrical connection comprises a second antenna portion in or on the header, wherein the power reception circuitry is configured to use the power current to provide power to the IMD.

In one example, the IMD further comprises one or more lead connectors in the header, a feedthrough between the header and the case, and a plurality of electrode feedthrough wires, wherein the electrode feedthrough wires connect to contacts in the lead connectors and pass through the feedthrough inside the case. In one example, the first electrical connection comprises a first feedthrough wire connected to the first antenna portion that passes through the feedthrough, wherein the second electrical connection comprises a second feedthrough wire connected to the second antenna portion that passes through the feedthrough. In one example, the first and second antenna portions are formed of a material of the case. In one example, the case comprises a planar surface configured to face an outside of a patient when implanted, wherein the first and second antenna portions are offset in or on the header towards the outside planar surface. In one example, the first antenna portion comprises a first end and a second end, and wherein the second antenna portion comprises a first end and a second end. In one example, the first electrical connection further comprises a first wire connected to the first end of the first antenna portion, wherein the second end of the first antenna portion is connected to the conductive case portion, wherein the second electrical connection further comprises a second wire connected to the first end of the second antenna portion, wherein the second end of the second antenna portion is connected to the conductive case portion. In one example, the first wire and the second wire pass through a feedthrough in the case. In one example, the first wire and the second wire are connected to the first ends of the first and second antenna portions through one or more openings in case. In one example, the case comprises a planar surface configured to face an outside of a patient when implanted, wherein the one or more openings are formed in the planar surface. In one example, the second ends of the first and second antenna portions are connected to a top of the case. In one example, the case comprises a planar surface configured to face an outside of a patient when implanted, wherein the second ends of the first and second antenna portions are connected to the planar surface. In one example, the power reception circuitry comprises a rectifier configured to convert the power current to a DC voltage that is used to provide power to the IMD. In one example, the IMD further comprises a battery within the case, wherein the power reception circuitry is configured to use the power current to provide power to the IMD to charge the battery. In one example, the conductive case portion comprises a conductive layer applied to the case. In one example, the conductive layer is also applied to the first and second antenna portions. In one example, the conductive layer is applied inside the case. In one example, the case comprises a window of material different from a material of the case, wherein a conductivity of the window material is less than a conductivity of the material of the case. In one example, the conductive case portion at least partially surrounds the window. In one example, the case comprises a planar surface configured to face an outside of a patient when implanted, wherein the window is formed in the planar surface. In one example, the power reception circuitry is not coupled to a wire-wound coil configured to receive the electromagnetic field.

An implantable medical device (IMD) configured to wirelessly receive power from an electromagnetic field is disclosed, which may comprise: a case housing control circuitry for the IMD, wherein at least a portion of the case is conductive, and wherein a case current is formed in the conductive case portion in response to the electromagnetic field; power reception circuitry inside the case; a nonconductive header affixed to the case; and first and second electrical connections to divert at least some of the case current as a power current to the power reception circuitry, wherein at least the electrical connection comprises a single antenna portion in or on the header, wherein the power reception circuitry is configured to use the power current to provide power to the IMD.

In one example, the IMD further comprises one or more lead connectors in the header, a feedthrough between the header and the case, and a plurality of electrode feedthrough wires, wherein the electrode feedthrough wires connect to contacts in the lead connectors and pass through the feedthrough inside the case. In one example, at least one of the first and second connections comprises a feedthrough wire connected to the single antenna portion that passes through the feedthrough. In one example, the single antenna portion is formed of a material of the case. In one example, the case comprises a planar surface configured to face an outside of a patient when implanted, wherein the single antenna portion is offset in or on the header towards the outside planar surface. In one example, the single antenna portion comprises only the first electrical connection but not the second electrical connection. In one example, the single antenna portion comprises a first end and a second end, wherein the first electrical connection further comprises a first wire connected to the first end of the single antenna portion, wherein the second end of the single antenna portion is connected to the conductive case portion. In one example, the second electrical connection comprises a second wire connected to the conductive case portion. In one example, the single antenna portion in or on the header comprises the first electrical connection and second electrical connection. In one example, the single antenna portion comprises a cross member connected to the conductive case portion along its length. In one example, the first electrical connection comprises a first wire connected to a first end of the single antenna portion, and wherein the second electrical connection comprises a second wire connected to a second end of the single antenna portion. In one example, the single antenna portion comprises a cross member connected to the conductive case portion at first contact and at a second contact, wherein there is a space between the cross member and the case between the first and second contacts. In one example, the first electrical connection comprises the first contact and a first wire connected to a first end of the single antenna portion, and wherein the second electrical connection comprises the second contact and a second wire connected to a second end of the single antenna portion. In one example, the power reception circuitry comprises a rectifier configured to convert the power current to a DC voltage that is used to provide power to the IMD. In one example, the IMD further comprises a battery within the case, wherein the power reception circuitry is configured to use the power current to provide power to the IMD to charge the battery. In one example, the conductive case portion comprises a conductive layer applied to the case. In one example, the conductive layer is also applied to the single antenna portions. In one example, the conductive layer is applied inside the case. In one example, the case comprises a window of material different from a material of the case, wherein a conductivity of the window material is less than a conductivity of the material of the case. In one example, the conductive case portion at least partially surrounds the window. In one example, the case comprises a planar surface configured to face an outside of a patient when implanted, wherein the window is formed in the planar surface. In one example, the power reception circuitry is not coupled to a wire-wound coil configured to receive the electromagnetic field.

An implantable medical device (IMD) configured to wirelessly receive from power an electromagnetic field is disclosed, which may comprise: a case housing control circuitry for the IMD, wherein at least a portion of the case is conductive, and wherein a case current is formed in the conductive case portion in response to the electromagnetic field; power reception circuitry inside the case; first and second electrical connections to divert at least some of the case current as a power current to the power reception circuitry, wherein the first electrical connection comprises a first contact made to the conductive case portion, and wherein the second electrical connection comprises a second contact made to the conductive case portion, wherein the power reception circuitry is configured to use the power current to provide power to the IMD.

In one example, the IMD further comprises a non-conductive header affixed to the case. In one example, the IMD further comprises one or more lead connectors in the header, a feedthrough between the header and the case, and a plurality of electrode feedthrough wires, wherein the electrode feedthrough wires connect to contacts in the lead connectors and pass through the feedthrough inside the case. In one example, the first and second connections are not formed in or on the header. In one example, the first electrical connection comprises a first wire connected to the conductive case portion at the first contact, and wherein the second electrical connection comprises a second wire connected to the conductive case portion at the second contact.

In one example, the first and second contacts are separated by a portion of the case having a first conductivity, and wherein the conductive case portion in which the case current is formed has a second conductivity higher than the first conductivity. In one example, the conductive case portion comprises a conductive layer applied to the case. In one example, the conductive layer is applied outside the case. In one example, the conductive layer is applied inside the case. In one example, the portion of the case having the first conductivity comprises a window of material different from a material of the case. In one example, the conductive case portion at least partially surrounds the window. In one example, the case comprises a planar surface configured to face an outside of a patient when implanted, wherein the window is formed in the planar surface. In one example, the window comprises a dielectric material, and the conductive case portion comprises a metallic material. In one example, the window and the conductive case portions comprise metallic materials. In one example, the first contact is made to an outside of the conductive case portion through an opening in the conductive case portion, and wherein the second contact is made to the outside of the conductive case portion through an opening in the conductive case portion. In one example, the first and contact contacts respectively include conductive pins. In one example, the first contact is made to an inside of the conductive case portion, and wherein the second contact is made to the inside of the conductive case portion. In one example, the power reception circuitry comprises a rectifier configured to convert the power current to a DC voltage that is used to provide power to the IMD. In one example, the IMD further comprises a battery within the case, wherein the power reception circuitry is configured to use the power current to provide power to the IMD to charge the battery. In one example, the IMD does not include a header. In one example, the case comprises a dielectric material, and wherein the conductive case portion comprises a conductive window. In one example, the dielectric material comprises a ceramic. In one example, the conductive window is affixed to the dielectric material in a manner to cover a hole in the dielectric material. In one example, the conductive window comprises a plate affixed on or in the dielectric material. In one example, the control circuitry further comprises stimulation circuitry to form stimulation currents at selected ones of a plurality of electrodes in contact with a patient's tissue, wherein the conductive window comprises one of the plurality of electrodes. In one example, the conductive window is configured to be in contact with a patient's tissue, and is further configured to operate as a case electrode. In one example, the power reception circuitry is not coupled to a wire-wound coil configured to receive the electromagnetic field.

BRIEF DESCRIPTION OF THE DRAWINGS

FIGS. 6A-6C show third examples of the improved IMD, which uses a single antenna portion.

DETAILED DESCRIPTION

Figures 1A, 1B:
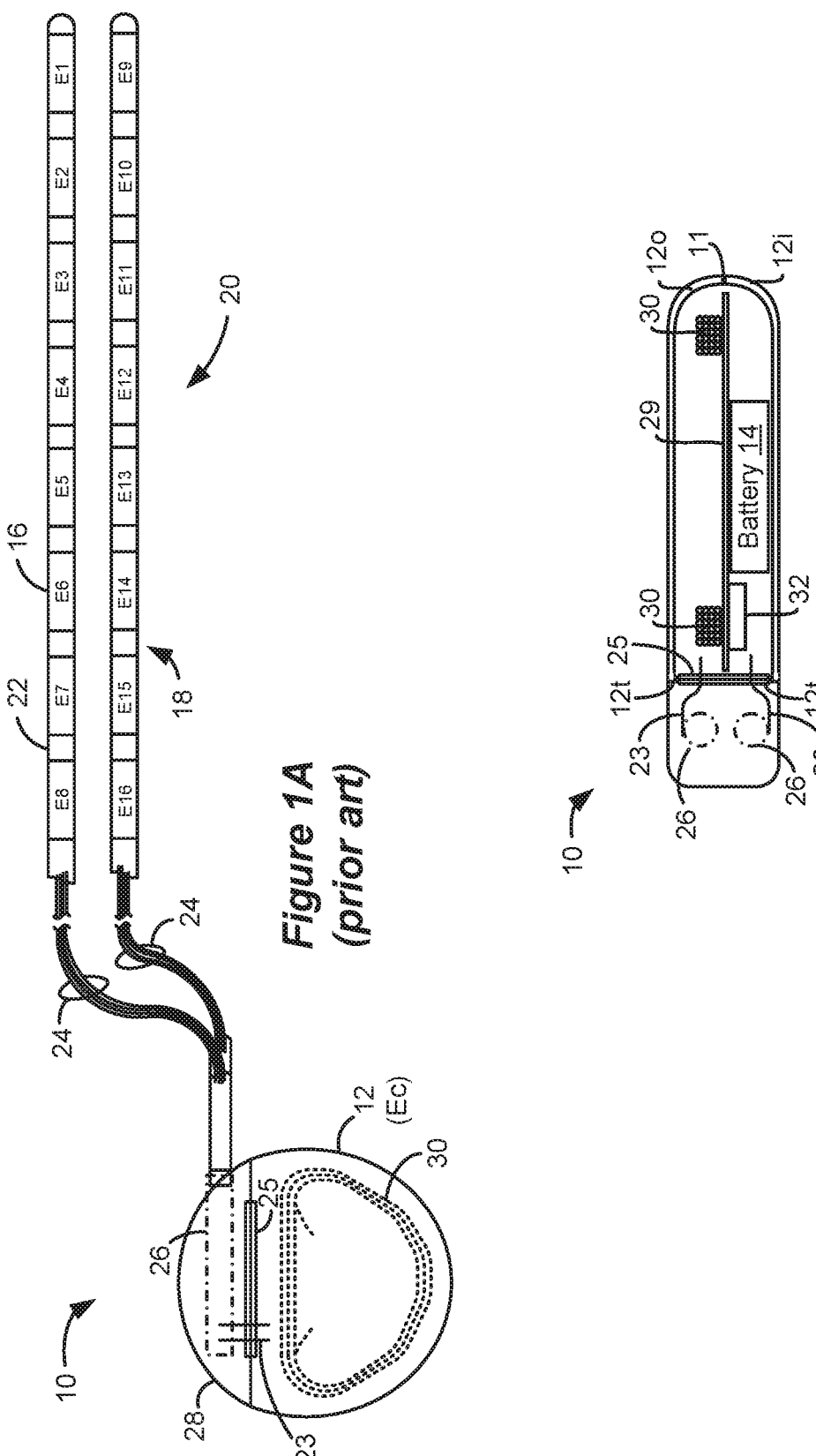
FIGS. 1A and 1B show different views of an implantable pulse generator, a type of implantable medical device (IMD), in accordance with the prior art.
Figures 2A, 2B:
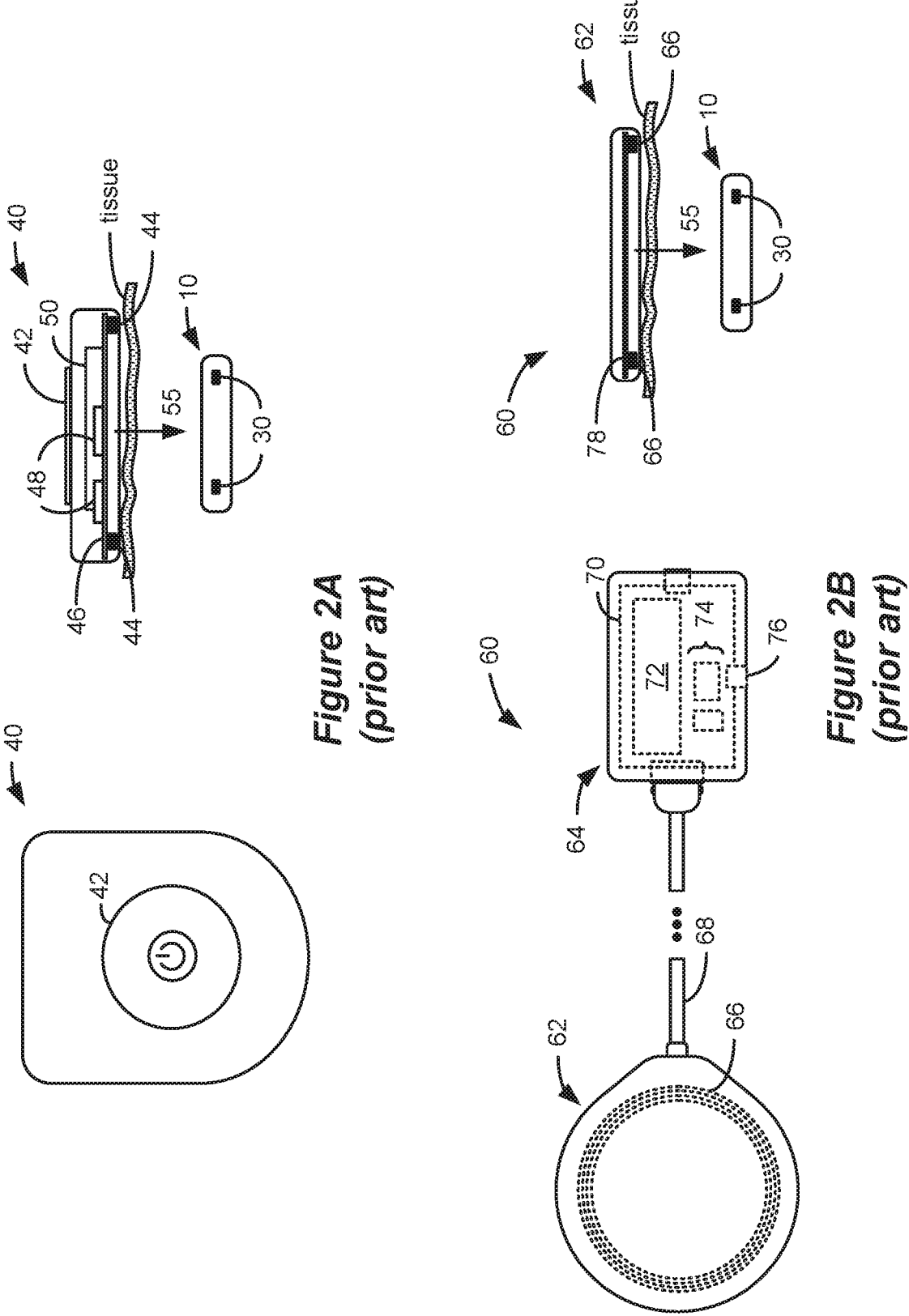
FIGS. 2A and 2B show different examples of external charger used to wirelessly charge a battery in an IMD or to provide power to the IMD.

The inventors see room for improvement in wireless charging of IMDs. In particular, the inventors find unfortunate that traditional IMDs like IMD 10 require a mechanically wire-wound secondary coil 30 to pick up the magnetic field 55. Such coils are relatively expensive, difficult to work with, and can suffer from reliability problems. Typically such charging coils 30 are made from multi-stranded copper Litz wire, which increases wire conductivity and improves AC performance, but is complicated and expensive. Such coils 30 are typically wound and formed on a mandrel prior to being assembled in the IMD 10. It can be difficult to connect the coil 30 to the PCB 29, and this connection can break and become unreliable. Further, a coil 30 can take significant volume in the IMD's case 12, which can hamper making IMDs 10 smaller and more convenient for patients. The inventors desire to provide an IMD that is capable of wirelessly receiving power from an external charger, but which does not include a wire-wound coil 30.

The inventors notice that the IMD 10's case 12 is typically conductive as already mentioned, and as such it is reactive to the incoming magnetic field 55. Specifically, the magnetic portion of the AC magnetic field 55 will induce AC Eddy currents in the case 12. As is known, Eddy currents comprise loops of electrical current induced within conductive materials, in accordance with Faraday's law of induction. Eddy currents flow in closed loops in planes perpendicular to the magnetic field 55, and as such will flow significantly in the outside case portion 12o of the IMD that faces the external charger. The magnitude of the current in a given loop is proportional to the strength of the magnetic field, the area of the loop, and the rate of change of flux, and is proportional to the conductivity of the material. Eddy currents flow in conductive materials with a skin depth, and as such are more prevalent at the outside surface of the outer case portion 12o that face the impinging magnetic field 55.

Eddy currents are generally viewed as an unwanted effect when charging an IMD. Some of the power in the field 55 is lost in the case 12 when Eddy current are induced, thus reducing the power that reaches the charging coil 30 inside the case. In short, the case 12 generally attenuates the power that is able to reach the coil 30 to useful effect to charge the IMD's battery 14. Further, Eddy currents generated in the case 12 are generally lost as heat, and thus charging by magnetic induction runs the risk that the case may overheat, which is a unique safety problem when one considers that the IMD 10 is designed for implantation inside of a patient.

Despite such conventional wisdom, it is the inventors' desire to provide an improved IMD which harnesses the power of Eddy currents generated at least in part in the IMD's case 12 during magnetic inductive charging, and to use such harnessed power to charge the IMD's battery 14 (or more generally to provide power to the IMD). In so doing, the inventors' improved IMD design does not require a wire-wound secondary charging coil 30, which alleviates manufacturing cost and complexity and reduces reliability issues inherent when using wire-wound coils. Further, the lack of a secondary charging coil 30 allows the IMDs to be made smaller and more convenient for patients.

Figures 3, 4A:
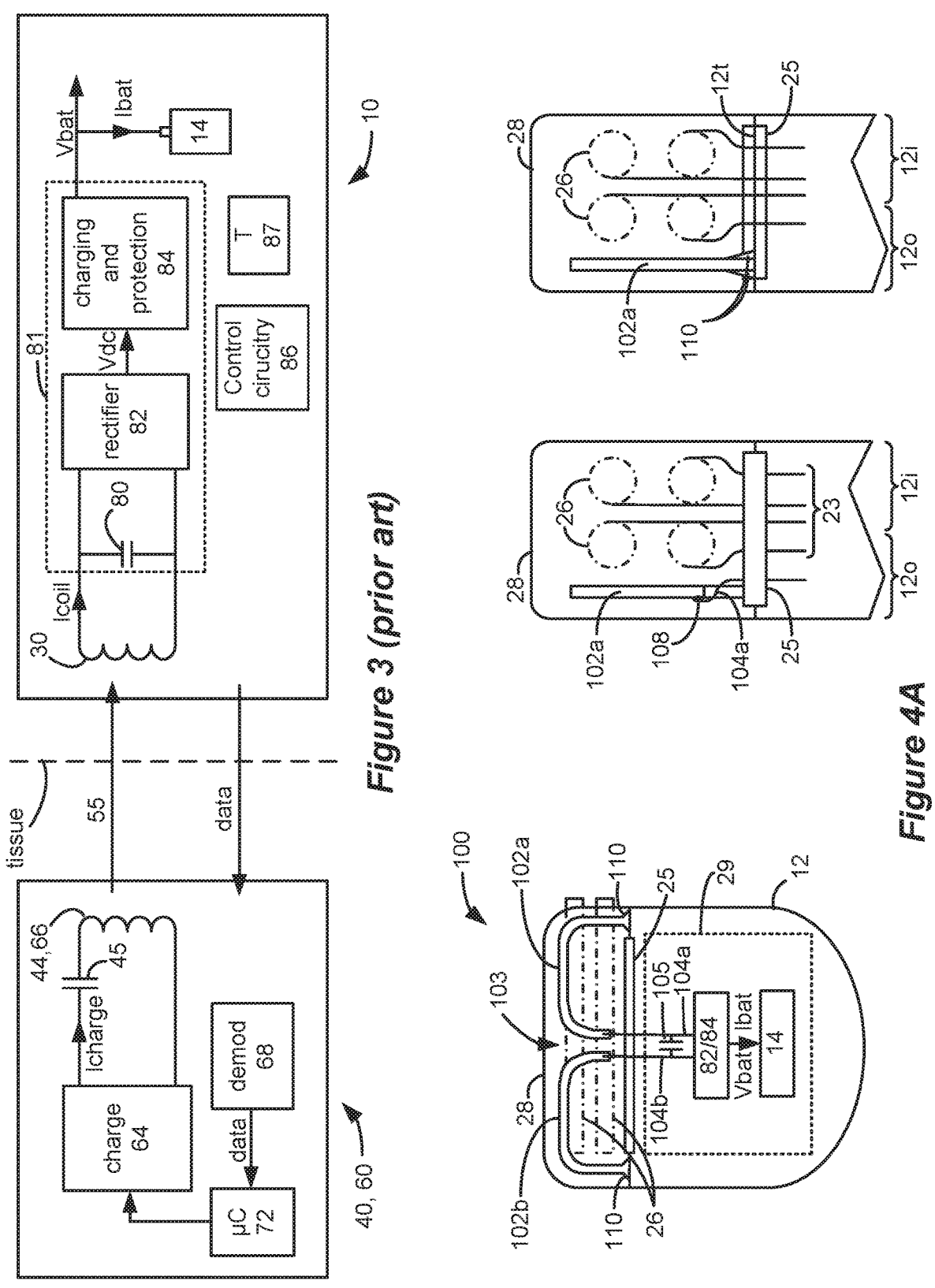
FIG. 3 shows relevant charging circuitry in the external chargers and the IMD, in accordance with the prior art.
FIGS. 4A-4D show first examples of an improved IMD without a wire-wound coil but capable of receiving wireless power from an external charger by harnessing Eddy currents generated in the IMD's conductive case, in which one or more antenna portions are provided in the IMD's header region.

A first example of such an improved IMD 100 is shown in FIG. 4A. In this example, antenna portions 102a and 102b are included within the IMD 100's header 28. It is useful to note at this point that such antenna portions are not strictly required in all embodiments, as explained later starting with FIG. 10A.

The antenna portions 102a and 102b are not wound coils, and are preferably not made of wire, although they could be. Instead, the antenna portions 102a and 102b are preferably formed from sheet metal into the shapes shown. The portions 102a and 102b are preferably conductive, and may be made from any number of conductive materials or alloys, such as those containing titanium, copper, gold, silver, and the like. The portions 102a and 102b may also include combinations of alloys formed in distinctive layers, and in this regard, the portions may be coated, plated, or cladded with conductive materials, as discussed further subsequently.

In the example of FIG. 4A, the antenna portions 102a and 102b are generally C-shaped, with outside ends attached to the case 12 (110), and with inside ends attached to antenna feedthrough wires 104a and 104b respectively. More specifically, and as shown in the cross sectional figure to the right, the outside ends of the portions 102a and 102b (only portion 102a is shown) are mechanically and electrically connected to the top surface 12t of the case, and more specifically to the top surface 12t of the outside case portion 12o. Such attachment may be made by welding or brazing the outside ends to the top surface 12t, as represented by weld 110. The left cross sectional figure shows the inside ends of the portions 102a and 102b (again, only 102a shown), and shows attachment of the inside ends to the antenna feedthrough wires 104a and 104b (only 104a shown), which attachments may be made via a solder or weld 108. In this example, the antenna feedthrough wires 104a and 104b pass through the same feedthrough 25 as the electrode feedthrough wires 23 that connect to the electrode contacts in the lead connectors 26. This example shows four lead connectors 26 arranged in a 2x2 fashion in the header 28, but more or fewer lead connectors could be used.

As shown in the cross sections of FIG. 4A, the antenna portions 102a and 102b are preferably offset in the header 28 towards the major surface of outside case portion 12o (to the left as shown) of the IMD 100, with the lead connectors 26 in the header being offset towards the major surface of the inside case portion 12i (to the right). This is preferred to bring the antenna portions 102a and 102b closer to the external charger's magnetic field 55, and to minimize interference of conductive structures in the lead connectors 26 with magnetic field reception. Once the lead connectors 26 are attached to the electrode feedthrough wires 23, and the antenna portions 102a and 102b are connected to the case 12 and to the antenna feedthrough wires 104a and 104b, the header 28 can be formed over these structures, such as by encapsulation or overmolding with a suitable header material, e.g., a polymer, epoxy, or thermoset plastic. However, it is not strictly necessary for proper functioning that the antenna portions 102a and 102b be located in the header 28, or encapsulated within the header material. For example, the antenna portions 102 and 102b may also extend from, or be on the outer surface of, the header 28. The header 28 may not include lead connectors in IMD designs that do not require leads.

Figure 4B:
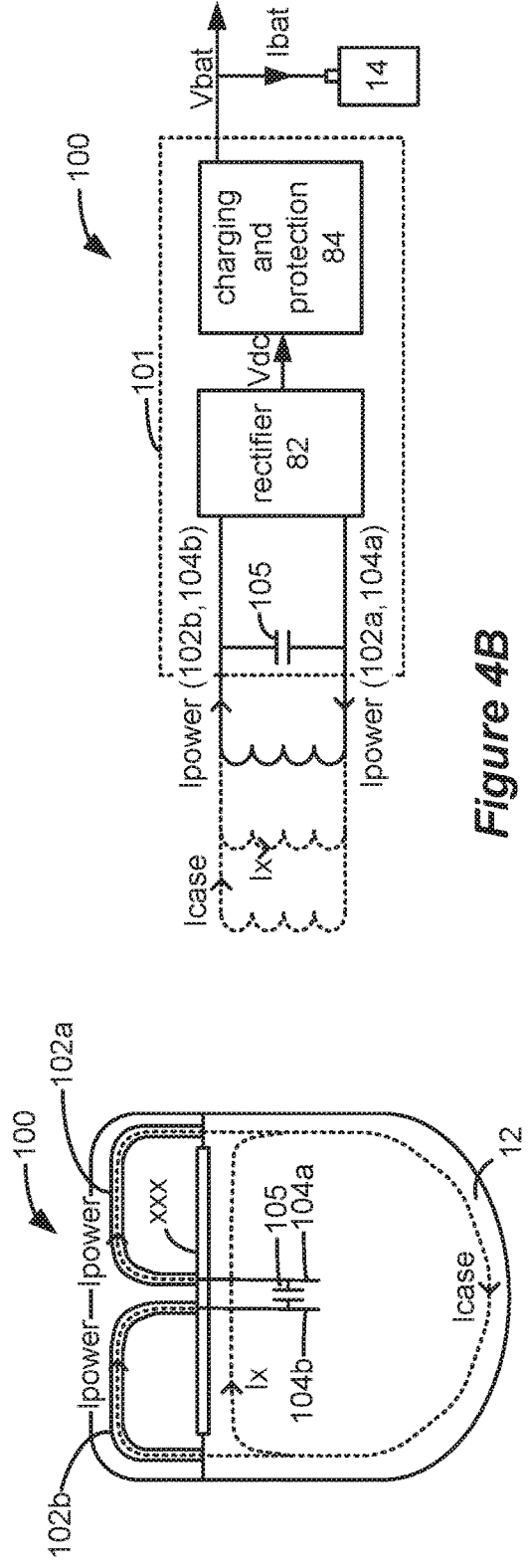

Further details of the circuitry and the formation of a current Ipower used to provide power to the IMD 100 are shown in FIG. 4B. As discussed above, the magnetic field 55 will induce Eddy currents in the conductive case 12. These circular currents will tend to oppose one another in the center of the case, but will reinforce each other towards the case's periphery, giving rise to a current, Icase, with a highest current density proximate to the periphery as shown. This current Icase would generally return as current Ix towards the top of the case.

However, at least some (and in other designs, possibly all) of the current Icase will also be diverted via the electrical connections 110 and to the antenna portions 102a and 102b as current Ipower. The flow of current Ipower is facilitated in different ways. First, the outside ends of the antenna portions 102a and 102b are connected (110) proximate to the periphery of case 12 where Icase is highest. Second, the antenna portions 102a and 102b are preferably formed of high conductivity (low resistance) materials, as described above. In this regard, it is preferable that the antenna portions 102a and 102b (e.g., silver) have a higher conductivity than the conductive material used to form the case (e.g., titanium), which bolsters the magnitude of Ipower relative to return current Ix. Third, as noted just discussed, the preference for Eddy currents to flow to the periphery of conductive structures means that current will preferably flow through the antenna portions 102a and 102b, which are more peripheral in the IMD 100 than the case portion where return current Ix is formed. In short, and through these means, a significant AC current Ipower is generated, which may be on the order of 0.5 to 3.0 Amps and suitable for charging the battery 14.

The antenna feedthrough wires 104a and 104b are connected to the antenna portions 102a and 102b, and are connected to the PCB 29 inside the case 12 to provide Ipower to power reception circuitry 101. Power reception circuitry 101 as before can include a tuning capacitor 105, which can be serially connected but is shown in parallel between the antenna feedthrough wires 104a and 104. The capacitance value of the tuning capacitor 105 can be modified to tune reception to the frequency of the magnetic field 55, as discussed further below. A rectifier 82 as before can derive a DC voltage Vdc, which can optionally be provided to charging and protection circuitry 84 used to derive Vbat and Ibat to charge the IMD 100's battery 14, or more generally to provide power to the IMD 100.

In short, first and second electrical connections divert at least some of Icase as Ipower, thus allowing the power reception circuitry 101 to use Ipower to provide power to the IMD. These electrical connections can include different structures, such as antenna portions, wires, contacts, or combinations of these, as explained in other various embodiments below.

Figure 4C:
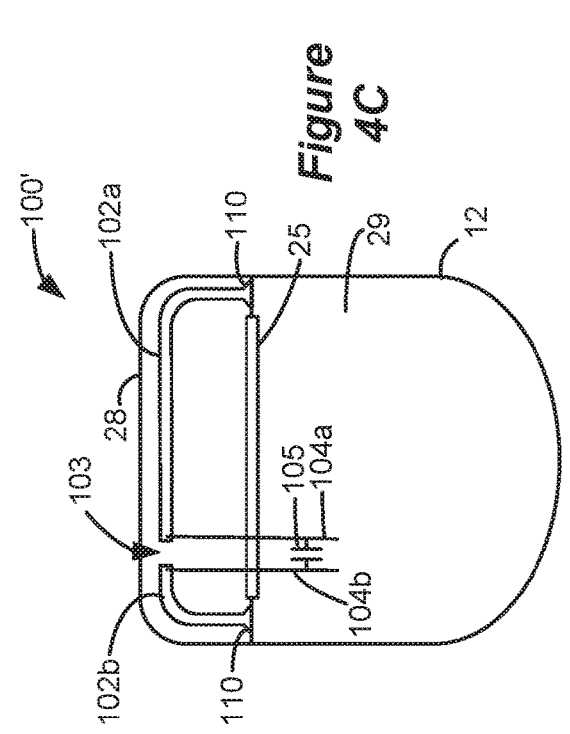

In the example of FIG. 4A, the antenna portions 102a and 102b are similarly sized, and include a gap 103 between them, which gap 103 is generally centered from left to right in the IMD 100. However, the antenna portions 102a and 102b may be of different sizes, and the gap 103 may be provided in different positions without affecting the current paths used to form Ipower. For example, in IMD 100' of FIG. 4C, the gap 103 has been moved to the left, and thus antenna portion 102b is smaller than antenna portion 102a.

Figures 4D, 5:
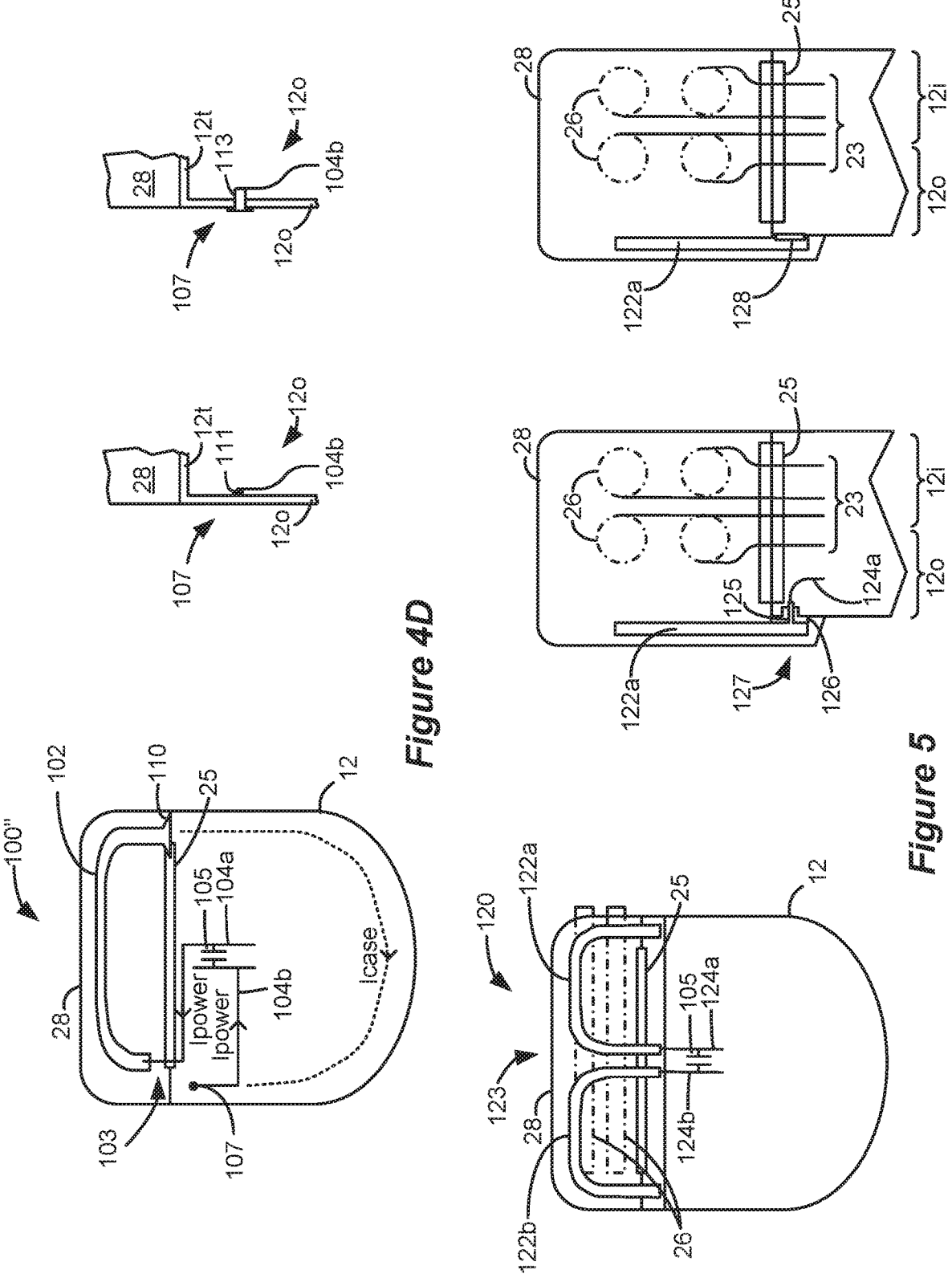
FIG. 5 shows a second example of the improved IMD, in which the antenna portions are differently connected to the IMD's case.

In IMD 100" of FIG. 4D, only a single antenna portion 102 is present in the header 28 region, having a right end affixed to the top surface 12t of the case (110), and having a free end attached to antenna feedthrough wire 104a as before. Antenna wire 104b in this example does not pass through the feedthrough 25, but instead is connected 107 to the outside case portion 12o. Such connection 107 can be established in different ways as shown in FIG. 4D's cross sections. In the left cross section, the antenna wire 104b is connected to the inside surface of the outside case portion 12o, i.e., inside the case, at a solder or weld 111. In the right cross section, the antenna wire 104b ultimately makes an electrical connection with the outside surface of the outside case portion 12o. This is facilitated by use of a conductive pin 113 which passes through an opening (not labeled) in the major surface of the outer case portion 12o. This pin 113 can be welded to the outside surface, and welded inside the case to the antenna wire 104b. Connection 107 in the right cross section may be preferred over the left cross section as more conducive to increasing the magnitude of Ipower. This is because Eddy currents as noted earlier will tend to form on the outside surface of the outside case portion 12o (via the skin depth phenomenon), which pin 113 in the right cross section connects to directly. When connection 107 is established on the inside surface as in the left cross section, the thickness of the outside case portion 12o intervenes between the Eddy currents on the outside surface and the connection 107 on the inside surface, creating a bulk resistance which could adversely affect the flow of Ipower. Extra steps may be desirable to ensure that connection 107 as shown in the right cross section is suitably hermetic to prevent fluid ingress. For example, and as discussed in other examples below, the pin 113 may be fixed in the opening in the outside case portion 12o using a glass ferrule, and/or the header 28 may be overmolded so as to cover the connection.

In any event, in IMD 140", and regardless of the means by which connection 107 is connected to the case 12, the circuit is effectively the same as described in FIG. 4B: some amount of Icase is provided to the capacitor 105 and related circuitry (not shown) as Ipower via antenna wire 104b, while antenna wire 104a and antenna portion 102 return Ipower back to Icase.

FIG. 5 shows another example of an improved IMD 120 having antenna portions 122a and 122b, which differs from the previous example in the manner in which the antenna portions are connected. In this example, and as best seen in the cross sections, the antenna portions 122a and 122b are connected to the major surface of the outside case portion 12o, rather than to the top surface 12t. The right cross section shows connection of the outside ends of the antenna portions (only 122a shown) at the periphery of the case, and shows that the outside ends have been welded (128) to the major surface of the outside case portion 12o to establish an electrical connection.

The left cross section shows the inside ends of the antenna portions (again only 122a shown). In this example, the inside ends do not connect to an antenna feedthrough wire that passes through the IMD's feedthrough 25 (compare 104a in FIG. 4A). Instead, a conductive path from the inside end passes through an opening 127 formed in the major surface of the outside case portion 12o. This can occur in different ways, but as shown, the inside end of antenna portion 122a includes or is connected to a conductive pin 125 which passes through the opening 127 in the outside case portion 12o. A glass ferrule 126 may intervene in the opening 127 between the pin 125 and the outside case portion 12o, and melted similar to the manner in which the electrode feedthrough wires 23 are traditionally hermetically affixed and insulated when passing through the feedthrough 25. The glass ferrule 126 insulates the signal at the inside ends from the case 12, and also provides a hermetic seal to prevent liquid ingress at the entry point of the pin 125. An antenna wire 124a (124b for antenna portion 122b) can then be connected to the pin 125 by soldering, welding or the like. As before the antenna wires 124a and 124b are connected to the PCB 29, the tuning capacitor 105, and the rectifier 82 and other circuitry 84, similar to what was described in FIGS. 4A and 4B.

Notice in the cross section of FIG. 5 that attaching the antenna portions 122a and 122b to or through the major surface of the outside case portion 12o may slightly increase the device's thickness, and as shown, it may be warranted to increase the thickness of the header 28 so that such structures can be encapsulated. Antenna portions 122a and 122b are as before separated by a gap 123, which is shown as centered in IMD 120. However, the position of this gap 123 can vary similarly to what was shown in FIGS. 4C and 4D, although such variations are not depicted for simplicity.

The manner in which the antenna portions are connected to the IMD can vary, and the approaches shown in FIGS. 4A and 5 can both be used together. For example, the outside ends of the antenna portions could be connected to the top surface 12t of the case 12 as shown in FIG. 4A, with the inside ends being connected through openings 127 in the major surface of the outside case portion 12o as shown in FIG. 5. Likewise, the outside ends can be connected to the major surface as shown in FIG. 5, while the inside ends being connected to antenna feedthrough wires that pass through the feedthrough 25 as shown in FIG. 4A.

FIG. 6A shows another example of an improved IMD 140, and in this example there is only a single antenna portion in the header 28. The antenna portion as before includes two C-shaped portions 142a and 142b, but also includes a cross member 145 which connects that on the bottom. In this example, the cross member 145 is affixed to the top surface 12t of the case 12 using a weld 110, similar to the manner in which the outside ends of antenna portions 102a and 102b were connected to the top of the case in FIG. 4A. The design of IMD 140 may be easier to manufacture because there is only a single antenna portion 142, and because that portion is connected to the case 12 along the length of the top surface 12t, making this connection more stable. Current nonetheless still flows similarly to what was described earlier with respect to FIG. 4B. At first glance, it may seem that the cross member 145 would act as a short circuit, sending all of current Icase through Ix, and thus reducing Ipower to zero. However, the above-explained tendency of Eddy currents to be forced to the periphery of conductive structures keeps this from occurring, such that Ipower still remains significant, and of a suitable magnitude to charge IMD 140's battery 14.

Although not shown, note that the antenna portion 142, and in particular its cross member 145, could also be attached to the major surface of the outer case portion 12o, as occurred in FIG. 5 (128), although this variation is not depicted. The inside ends of the antenna portion 142 can be connected to antenna feedthrough wires 144a and 144b that pass through the feedthrough 25 as depicted (e.g., FIG. 4A), or may connect to the circuitry through openings (127) in the outer case portion 12o (as shown in FIG. 5). A gap 143 between the antenna portions 142a and 142b can also be moved to different locations (see, e.g., FIGS. 4C and 4D), and IMD 140' of FIG. 6B shows an example where gap 143 has been moved to the left. Note that antenna wire 144b is shown as connecting to the cross member through the feedthrough, but it could also connect to the case as was shown in FIG. 4D.

FIG. 6C shows another example of an improved IMD 140" in which antenna portions 142a and 142b are connected by a cross member 145. However, in this example, the cross member 145 is not connected to the case 12 (e.g., the top surface 12t) along its length. Instead, the cross member 145 is connected at left and right ends, using welds 110 in this example. This leaves a space 147 between the cross member 145 and the case 12. This space 147 would be filled with the header 28 material, or could also be left as an air gap within the header 28. Experimentation shows that use of a space 147 increases the inductance in the Ipower current path, meaning that a lower Ipower will build a higher voltage across the capacitor 105 and rectifier 82, thus rendering the circuit more efficient to deliver power the IMD 140".

Figures 7, 8, 9:
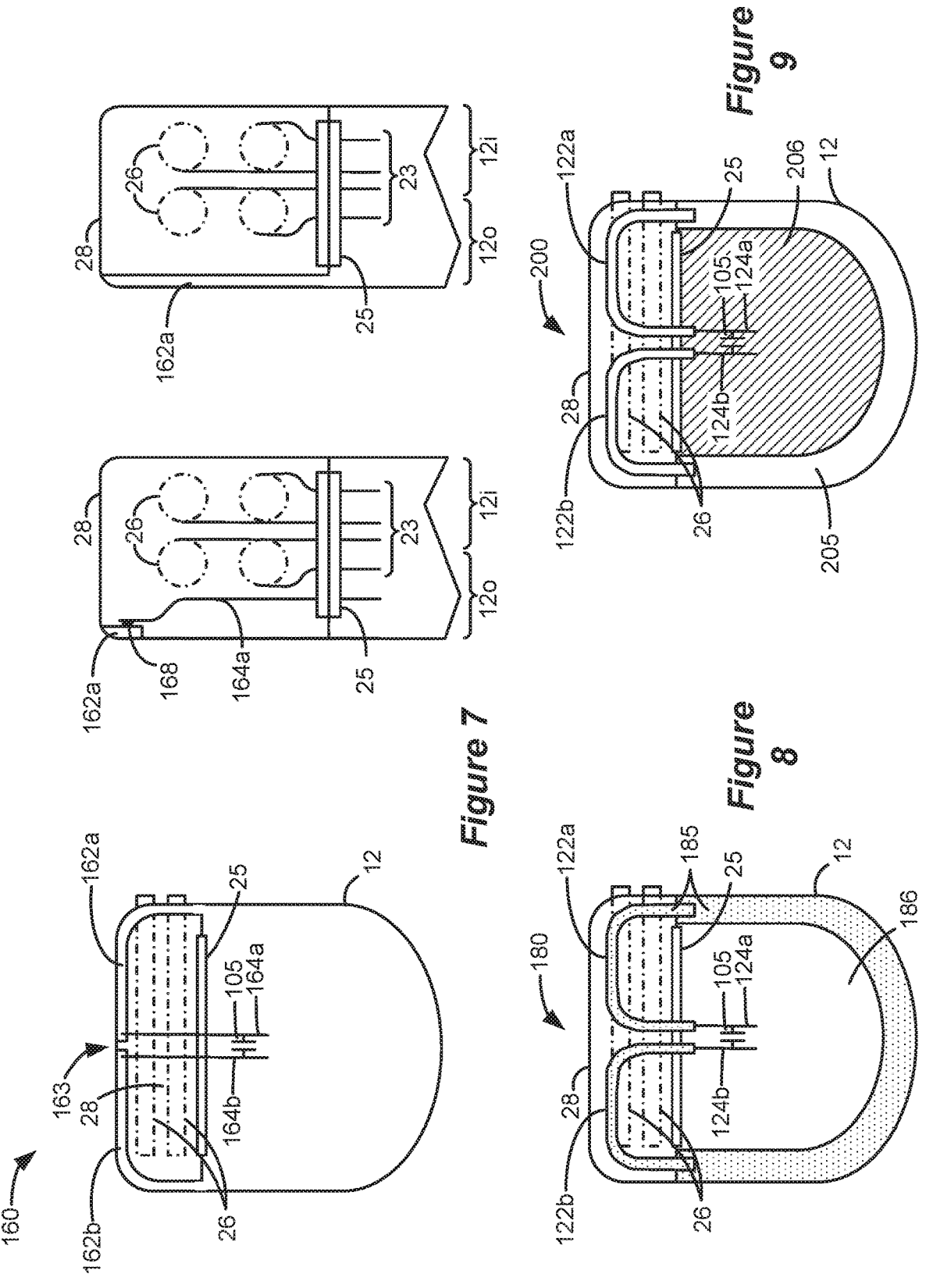
FIG. 7 shows a fourth example of the improved IMD, in which the antenna portions are formed using the material of the case.
FIG. 8 shows a fifth example of the improved IMD, in which a conductive layer is used to accentuate the flow of Eddy currents.
FIG. 9 shows a sixth example of the improved IMD, in which a lower-conductivity window in the case is used to accentuate the flow of Eddy currents.

FIG. 7 shows another example of an improved IMD 160. In this example, the antenna portions 162a and 162b are not formed of separate structures, but are instead formed using the material of the case 12 itself. Specifically, the conductive material of the outside case portion 12o continues into the header 28 region, thus forming antenna portions 162a and 162b having a gap 163 between them. The material of the inside case portion 12i could also continue into the header region if desired, although this isn't shown. The right cross section shows the assent of the antenna portion 162a from the outer case portion 12o into the header 28 region, while the left cross section shows connection (168) of the inside end to an antenna feedthrough wire 164a that passes through the feedthrough 25 as in FIG. 4A. This inside end could also connect through an opening in the outside case portion 12o (not shown), as shown in FIG. 5. Once the structures are connected, the header material 28 may be formed within the antenna portions 162a and 162b via mold injection, and although not shown the header material 28 may also fully encompass or encapsulate these portions. Current Ipower, and charging of IMD 160's battery 14, would occur as explained earlier. As occurred in earlier examples, the position of gap 163 between the antenna portions 162a and 162b can be varied.

FIG. 8 shows another example of an improved IMD 180. In this example, the conductivity of the current paths carrying Icase and Ipower are increased by the application of a conductive layer 185. This conductive layer 185 is applied as shown to the periphery of the case 12, and in particular to the periphery of the major surface of the outer case portion 12o where Icase will tend to form. The conductive layer 185 preferably comprises a material that is more conductive than the material used to form the outside case portion 12o, and as such the conductive layer 185 circles a region 186 in the middle of the outside case portion 12o that is less conductive. This promotes the conduction of Icase (FIG. 4B) in response to Eddy currents induced by the magnetic field 55. Additionally, the conductive layer 185 can also be applied to the antenna portions 122a and 122b, which promotes the conduction of Ipower. (The example of FIG. 8 builds on the example of FIG. 5, but conductive layer 185 could also be applied to any of the previously described examples as well, although such variations are not depicted for simplicity).

The conductive layer 185 can be formed in different ways. For example, the region 186 and other important structures (e.g., the lead connectors 26) can be masked, and conductive layer 185 formed by sputtering, Chemical Vapor Deposition (CVD), electroplating, and like techniques. Conductive layer 185 may also comprise an applied cladding layer. Note that conductive layer 185 can be applied once relevant parts of the IMD 180 are assembled, or can be applied to the various pieces (12o, 122a, 122b) individually before they are assembled into the IMD 180. Conductive layer 185 can comprise any number of conductive materials, such as copper, gold, silver, and the like, or mixtures of different compounds, and can be formed with a thickness suitable to promote the flow of currents Icase and Ipower. While FIG. 8 shows the conductive layer 185 as formed on the both the outside case portions 12o and the antenna portions 122a and 122b, this layer could be formed only on one of these structures. For example, if the antenna portions 122a and 122b are already formed of suitably conductive materials, it may only be necessary to apply conductive layer 185 to the outside case portion 12o. To the extent conductive layer 185 is not biocompatible, it can be coated or even covered by header material, but this detail isn't shown.

Application of the conductive layer 185 means that the case 12 may be formed of different materials from the titanium alloys that are typically used. For example, the case 12 in the example of FIG. 8 may be formed of a dielectric material, such as ceramic, glass, epoxy or various plastics. While such a material is generally not susceptible to the formation of Eddy currents in response to the magnetic field 55, conductive layer 185 will allow Eddy currents to flow, thus ultimately providing currents Icase and Ipower needed for IMD power and charging.

FIG. 9 shows another example of an improved IMD 200 that is similar in function to the IMD 180 of FIG. 8 in promoting the conduction of Icase and Ipower by increasing the conductivity in regions where they flow. (Again, this example builds on the example of FIG. 5, but could be applied to any of the previously described examples). However, in this example, different materials are used to form the outside case portion 12o, leading to a conductivity difference which again promotes the flow of currents Icase and Ipower. Specifically, the outside case portion 12o includes a "window" 206 formed of a separate material from the rest of the outside case portion 12o. Window 206 is formed of a material with a lower conductivity than the rest of the outside case portion 12o, and preferably also lower than the conductivity of the antenna portions 122a and 122b. This promotes the flow of current Icase relative to return current Ix (FIG. 4B) in portions 205 of the outside case portion 12o that are formed of the higher conductivity case material, which in turn increases Ipower.

In one example, the window 206 can comprise a dielectric material, such as a ceramic, glass, epoxy or various plastics. In another example, the window 206 may comprise a metallic structure or alloy, but one with a lower conductivity used for the rest of the case 12 or the outside case portion 12o. For example, the window 206 may be formed of a lower conductivity Titanium-Aluminum-Vanadium alloy such as Ti-6Al-4V (e.g., Grades 5 or 23), while the remainder of the case 12 or outside case portion 12o is formed of higher conductivity pure titanium (e.g., Grade 1). Brazing, laser welding, or like techniques can be used to affix the window 206 within a hole formed in the outside case portion 12o. Preferably, the conductivity of the material used for the window 206 is three or less times lower than the conductivity of the material used for the remainder of the case 12 or outside case portion 12o. Although not shown, the conductivity difference between window 206 and portions carrying Ipower and Icase can be further accentuated by the application of a conductive layer 185, as occurred in FIG. 8.

Figures 10A, 10B:
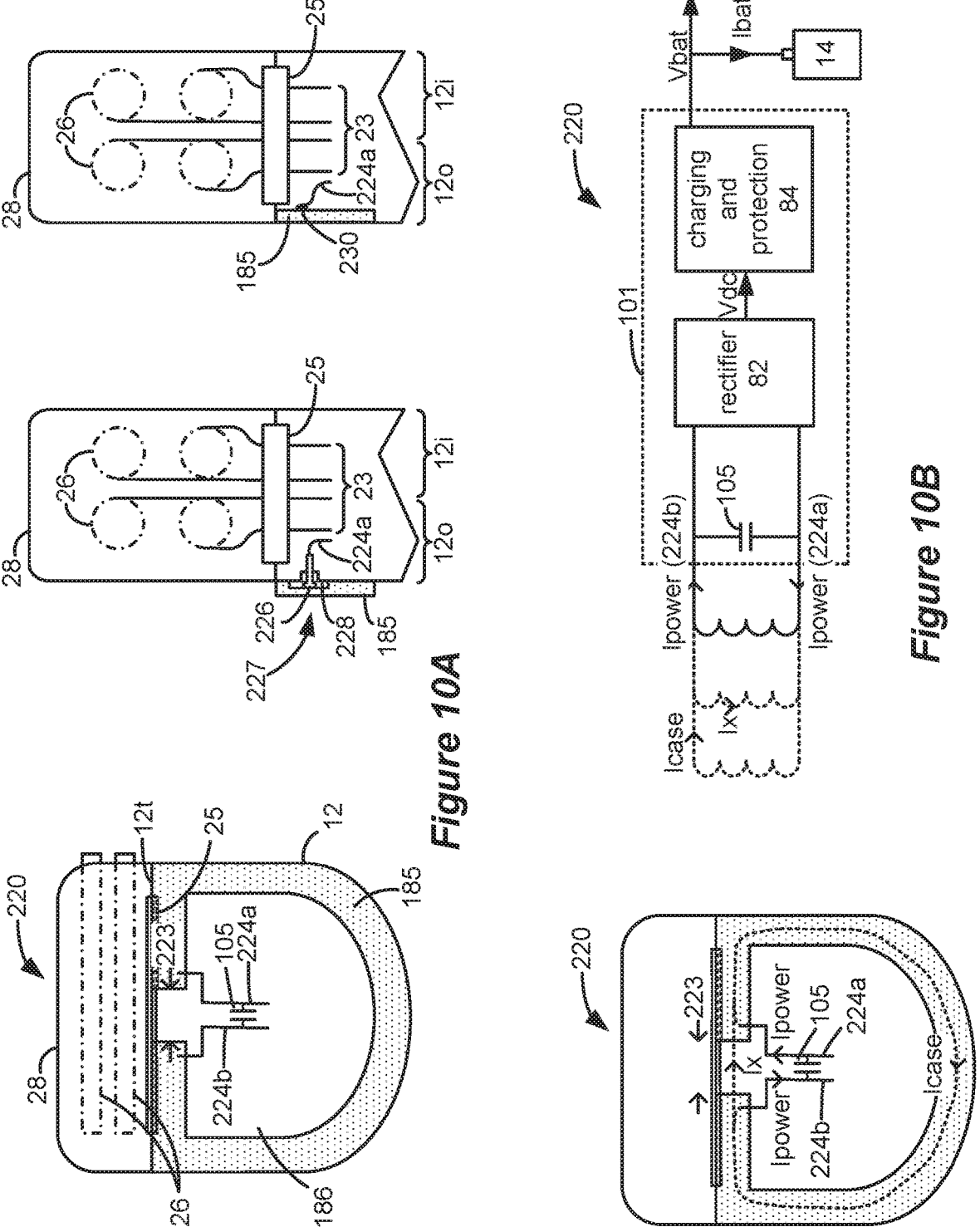
FIGS. 10A and 10B show a seventh example of the improved IMD, which does not use antenna portions in the header region, but which uses a conductive layer to accentuate the flow of Eddy currents.

FIGS. 10A and 10B shows another example of an improved IMD 220, which like other examples harnesses Eddy currents in the case 12 to promote IMD power and charging. However, in this example there are no antenna portions provided in the header 28 region of the IMD, and the header 28 can be formed as in traditional designs. Instead, relevant currents Icase and Ipower are generated entirely using the case, as explained further with respect to FIG. 10B. In the example of FIG. 10A, a conductive layer 185 is provided which is positioned around a portion of the periphery of the case. Specifically, conductive layer 185 is formed on the outside case portion 12o and in particular on its major surface around the periphery, and along a portion proximate to the top surface 12t, leaving a gap 223. The conductive layer 185 may be formed as earlier described with respect to FIG. 8, and may be formed of the same materials. The conductive layer 185 again preferably comprises a material that is more conductive than the material used to form the outside case portion 12o, and as such the conductive layer circles a region 186 in the middle of the outside case portion 12o and in the gap 223 that is less conductive.

FIG. 10B shows the relevant currents Icase, Ix, and Ipower that are formed in IMD 220. In this example, Icase is formed via Eddy currents as explained earlier in response to the magnetic field 55, with Icase preferentially forming in the conductive layer 185. Return current Ix occurs in the gap 223, and is thus formed within the lower conductance of the material of the outer case portion 12o. Antenna wires 224a and 224b provide electrical connections to the conductive layer 185 proximate to the gap 223 as explained shortly, and thus divert at least some of Icase as Ipower. Antenna wires 224a and 224b carrying Ipower as before are connected to power reception circuitry 101, which can be the same as described earlier.

FIG. 10A shows different ways that conductive layer 185 can be formed and connected to the antenna wires 224a and 224b (only connection to 224a is shown). In the left cross section, the conductive layer 185 is formed on the outside of the outside case portion 12o. The thickness of the conductive layer 185 is exaggerated for easier viewing. Connection of the conductive layer 185 to the antenna wire 224a is made through an opening 227 in the outside case portion 12o. While the wires 224a and 224b could connect directly to the conductive layer 185, in the depicted example a conductive pin 226 is used as an intermediary, and is positioned in the opening 227 and surrounded by a glass ferrule 228, which as before is useful for to provide hermeticity and prevent fluid ingress. One end of the pin 226 is connected to the antenna wire 224a inside the case 12, while an outside end of the pin 226 is exposed to contact the conductive layer 185 after it is applied. Although not shown, note that the material of the header 28 could be overmolded so as to cover the conductive layer 185 and in particular the openings 227 to further promote hermeticity. A pin 226 can also be used without a glass ferrule, similar to what was described earlier with respect to FIG. 4D.

In the right cross section, the conductive layer 185 is formed on the inside of the outside case portion 12o, such that the conductive layer 185 is inside the case 12. In the example, there is no need for an opening 227 to be provided in the outside case portion 12o, and instead the antenna wire 224a can be connected directly to the conductive layer 185 at a suitable connection 230, such as by welding or soldering. As was also true with respect to the example of FIG. 8, application of the conductive layer 185 means that the case 12 may be formed of different materials, and could be formed of a dielectric material as explained earlier. Use of a dielectric case material may be preferred in the example shown in the right cross section where the conductive layer 185 is inside the case; if the case 12 material was conductive, Eddy currents would form on the outside surface, with a bulk resistance—the thickness of the outside case portion 12o—intervening between the Eddy currents and the conductive layer 185 as explained earlier with reference to FIG. 4D. This would not be an issue if the case material is a dielectric, as Eddy currents would form directly in the conductive layer 185.

Figure 11:
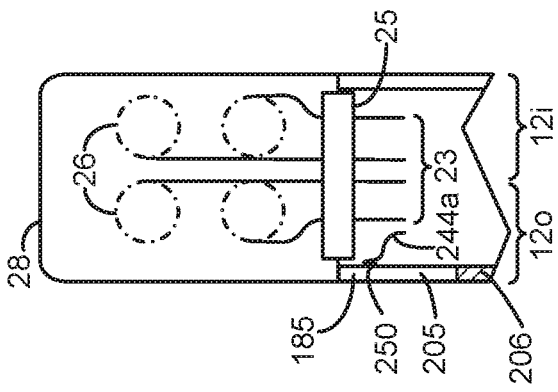
FIG. 11 shows an eighth example of the improved IMD, which does not use antenna portions in the header region, but which uses a lower-conductivity window in the case to accentuate the flow of Eddy currents.
Figure 11:
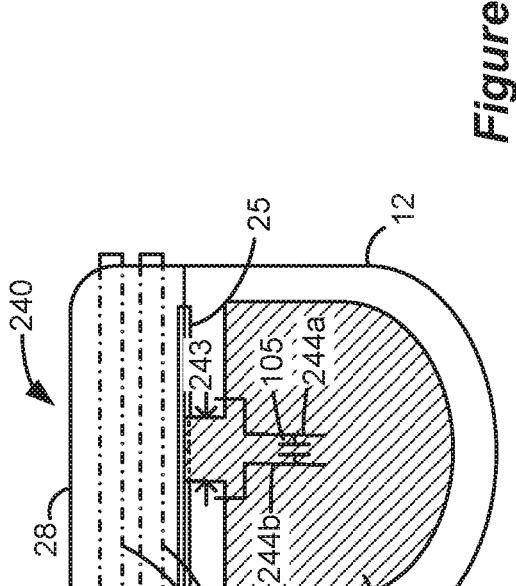

FIG. 11 shows another example of an improved IMD 240. Like IMD 220, IMD 240 does not use antenna portions in the header 28 region, and relevant currents Icase, Ipower, and Ix are generated entirely using the case 12, similar to what was explained with reference to FIG. 10B. However, in this example, the outside case portion 12o includes a window 206 of lower conductance material formed of a separate material from the rest of the outside case portion 12o, similar to what was described in FIG. 9. Lower-conductivity window 206 is preferably also present in a gap 243, similar to gap 223 of FIG. 10A, which promotes the flow of currents Icase and Ipower relative to return current Ix (FIG. 10B) in portions 205 that are formed of the higher conductivity case material. In this example, the antenna wires 244a and 244b contact the higher conductivity case portion 205 proximate to the gap 243. Such contact can be made outside of the case 12 (see, e.g., FIG. 4D), or the antenna wires 224a and 224b can connect to the inside of the outside case portion 12o at connections 250 as shown. As was true for the example of FIG. 9, the window 206 can comprise a dielectric material, or a metallic structure or alloy, but one with a lower conductance than is used for the rest of the case 12 or the outside case portion 12o.

Figure 12A:
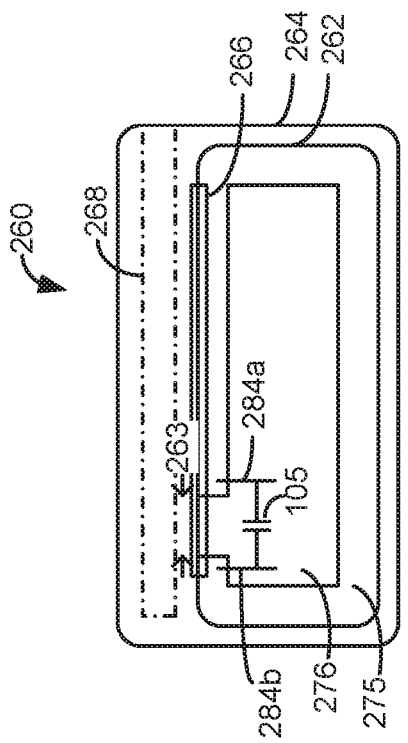
FIGS. 12A-12C show ninth examples of the improved IMD in a small form factor.

FIG. 12A shows another example of an improved IMD 260 without a wire-wound charging coil which as in other examples uses the case 262 to form necessary currents to derive power from the magnetic field 55. IMD 260 has a small form factor, and may be as described in U.S. Patent Application Publication 2017/0151440. IMD 260 may be significantly smaller than the IMD examples illustrated to this point. Note that application of the disclosed techniques—which do not require wire-wound charging coils 30—greatly facilitates the manufacture of smaller IMDs such as IMD 260.

IMD 260 includes a case 262 containing relevant electronics such as the battery and stimulation circuitry (not shown). One or more lead connectors 268 are formed outside of the case 262 and are connected via electrode feedthrough wires (not shown) to the circuitry inside the case via a feedthrough 266, similar to earlier examples. In this example, the case 262 and lead connector(s) 268 can be overmolded with a dielectric material 264 such as silicone, although epoxy of other materials could be used as well. The case 262 in this example includes a higher conductivity region 275 around its periphery, which surrounds a lower conductivity region 276. As in the examples of FIGS. 10A and 11, the lower conductivity region 276 includes a gap 263, which as explained earlier is useful to inhibiting return current Ix, and thus encouraging the flow of Ipower through antenna wires 284a and 284b. Higher and lower conductivity regions 275 and 276 can be made in any of the manners previously described with respect to FIGS. 10A-11, such as by use of a higher conductivity layer 185 or a lower conductivity window 206, and the case 262 may include or comprise dielectric materials. IMD 260 could also include antenna portions in the header portion proximate to the lead connector(s) 268 as in earlier examples, although this isn't shown.

Figure 12B:
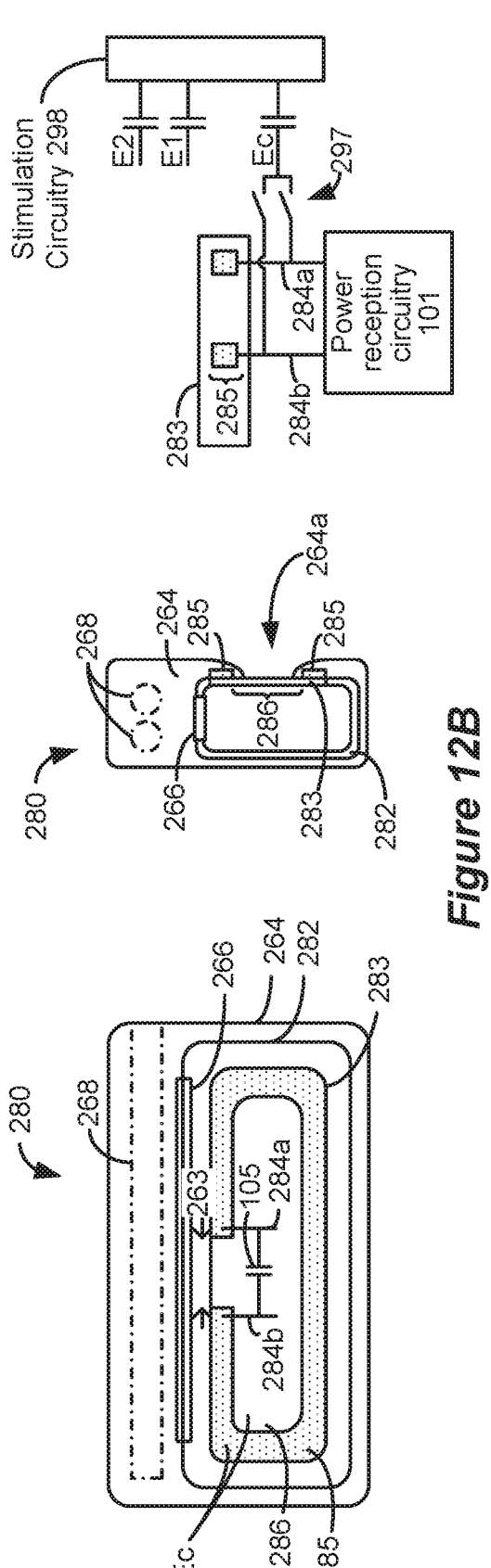

FIG. 12B shows a more particular example of an improved IMD 280 with a similar form factor to the IMD 260 of FIG. 12A. IMD 280 as before includes one or more lead connectors 268, a feedthrough 266, and an overmolded dielectric material 264. However, the case is formed of different materials. The majority of the case is comprised of a dielectric material 282 such as a ceramic. Included on one of the major surfaces of the case is a conductive material 283, which can comprise a conductive window attached to the dielectric case material 282, as best shown in the cross section. The conductive window 283 can be brazed to the ceramic case material 282.

In this example, the conductive window 283 serves a dual purpose. First, and as in other examples, the conductive window 283 serves as the means to receive the magnetic field 55 for IMD 280 powering and battery charging. In this regard, the conductive window 283 can as in earlier examples include a higher conductive region 285 around its periphery, and a lower conductivity region 286 in its center which includes a gap 263 as useful to generating Ipower as provided to the power reception circuitry. As in earlier example, higher and lower conductivity regions 285 and 286 can be formed in different ways. They may be formed of different materials (e.g., different alloys), or the conductivity of region 285 can be enhanced though the use of a conductive layer. The conductive layer can as before be placed on the outside or inside of the conductive window 283, with antenna wires 284a and 284b connected appropriately, similar to what was explained earlier for FIG. 10A. In FIG. 12A, a conductive layer is applied to the outside of the conductive window, with its thickness exaggerated in the cross section.

The conductive window 283 can also serve the purpose of acting as a case electrode, Ec. As one skilled in the art understands, using a case electrode during neurostimulation is particularly useful to provide a return current path for simulation currents formed at the electrodes Ex (e.g., on the leads), in what is commonly known as a monopolar mode of stimulation. Stimulation circuitry 298 in the case, used to provide simulation currents to selected ones of the electrodes Ex, can connect to the conductive window 283 to form the case electrode Ec. Such connection may be made to either the higher or lower conductivity regions 285 or 286, and would typically be made by a wire connected to the inside of the case. As best seen in the cross section, the overmolded dielectric material 264 can be formed with an opening 264a, thus allowing the outside of the conductive window 283 to be in physical and electrical contact with a patient's tissue.

In the example circuitry shown in FIG. 12B, one or more of the antenna wires 284a and 284b, otherwise used to connect the power reception circuitry 101 to the conductive region 285, can also be used to operate the conductive window 283 as a case electrode. This can occur in different ways, but in the example shown, one or more switches 297 are connected between the case electrode output Ec of the stimulation circuitry 298 and one or more of the antenna wires 284*a* and 284*b*. (In reality, there would only need to be one switch 297 connected to either of 284*a* or 284*b*, but two switches connected to both are shown). Logic (e.g., the IMD's control circuitry 86, FIG. 3), can control the switch (es) 297, such that they are open when the IMD 280 is receiving a magnetic field, and closed when the stimulation circuitry 298 is being used to drive the conductive window 283 as a case electrode. This approach of using one or more of the antenna wires 284*a* and 284*b*, while not necessary, is favored because it allows the conductive window 283 to operate as the case electrode without the need of providing an extra connection to the conductive window 283 for the case electrode beyond the antenna wires.

Figure 12C:
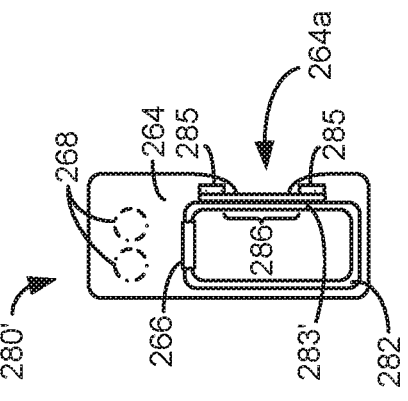

FIG. 12C shows in cross section an alternative to IMD 280 (IMD 280') in which the conductive feature 284 does not comprise a conductive window 283 positionable in a hole in the dielectric case 282, but instead comprises a conductive plate 283' positionable on or in the case. In the example of FIG. 12C, the conductive plate 283' has been positioned on the outside of the dielectric case 282, thus allowing it to be used as a case electrode Ec as just explained. However, the conductive plate 283' could also be placed on the inside of the dielectric case 282 as well. The conductive plate 283' can as before have higher and lower conductive regions 285 and 286 as explained with respect to FIG. 12B. Although not shown, openings in the dielectric case 282 can allow connection of the antenna wires 284*a* and 284*b* to the higher conductive regions 285, as occurred in earlier examples. For purposes of this disclosure, a "plate" such as 283' can be considered as a type of "window" such as 283, and as such a window 283 or 283' can be placed in a hole in the case 282 (FIG. 12B), or on or in a case 282 that doesn't have a corresponding hole (FIG. 12C).

Note that a conductive plate such as 283' affixed on or in a case could be used in previously-introduced examples as well. For example, a conductive plate affixed on or in the case can comprise the conductive layer 185 in FIGS. 8 and 10A.

While it is useful in the examples to form a case electrode using the same conductive window 283 or plate 283' used for power reception, note that this is not strictly necessary. A different conductive window, plate, or other electrode formed in conjunction with the case could be used as a case electrode separate from the conductive window 283 or plate 283' used for power reception.

Figures 13, 14:
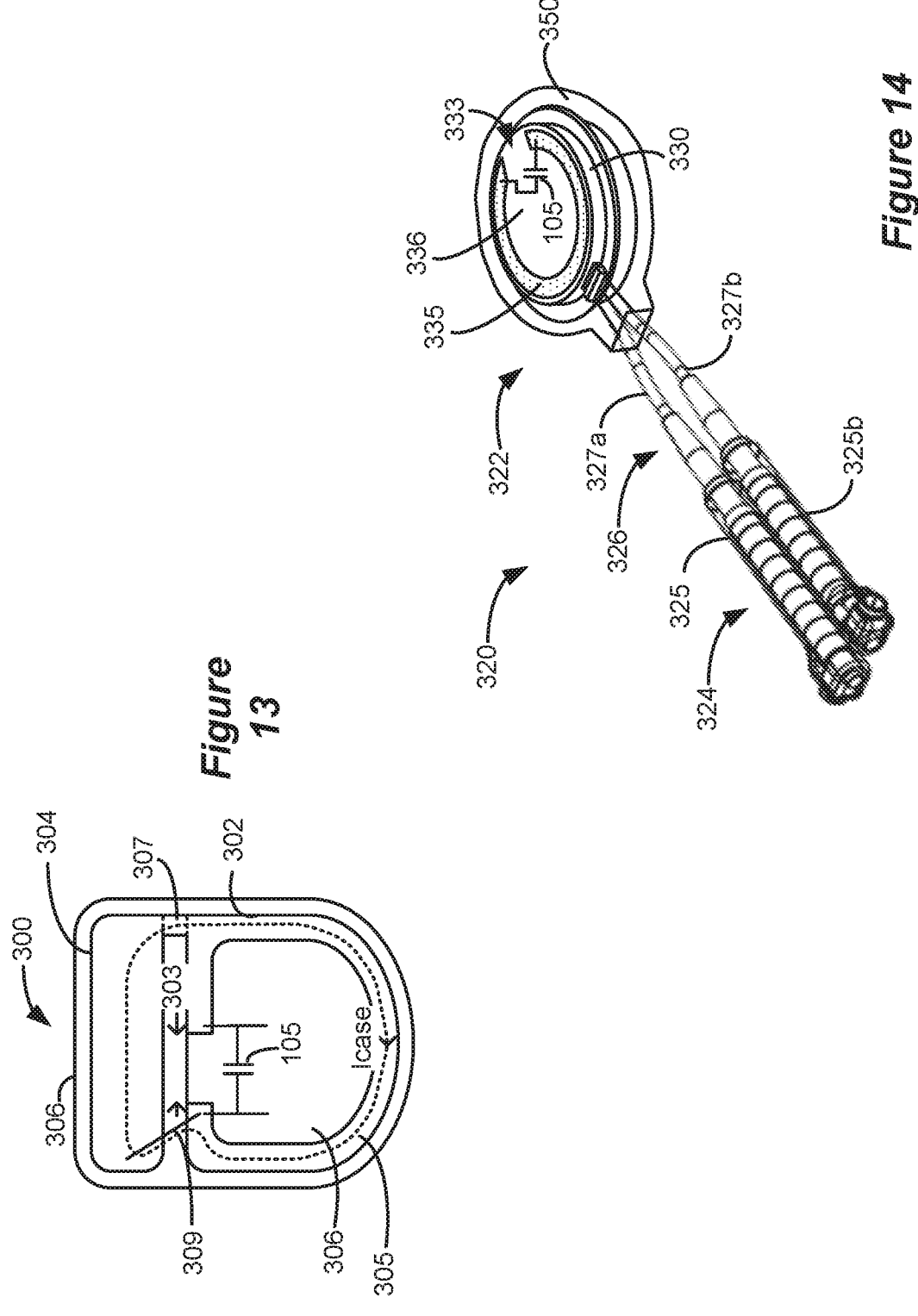
FIG. 13 shows a tenth example of the improved IMD, which includes two conductive case modules.
FIG. 14 shows an eleventh example of the improved IMD, which lacks a header attached to the case.

FIG. 13 shows another example of an improved IMD 300. In this example, the case is separated into different case modules 302 and 304, which are encompassed within an overmold 306. Lead connectors are not shown in this example for simplicity, but could be incorporated into the overmold 306 with signaling ported into the case module 302 in any number of different ways. In this example, the case modules 302 and 304 house different circuitry of the IMD 300. For example, case module 302 may comprise stimulation circuitry and other electronics, while case module 304 may house the battery 14 (not shown). The electrical circuitry of IMD 300 can be split between the two case modules 302 and 304 in any desired fashion.

In this example, the case modules 302 and 304 are formed and connected in a manner to promote the flow of Icase, which as before is tapped as Ipower to provide power or to charge the IMD 300's battery 14. To promote current Icase, case module 302 preferably includes higher conductivity region 305 around its periphery, which surrounds at least in part a lower conductivity region 306. As was the case in earlier examples, higher and lower conductivity regions 305 and 306 can be formed in different manners, such as by use of a conductive layer 185 (FIG. 8) or a lower conductivity window 206 (FIG. 9), although such details aren't shown. Case module 304 is preferably of higher conductivity, and is connected to higher conductivity region 305 in case module 282 to promote the flow of Icase as shown. To promote such flow, case modules 302 and 304 are connected together by different means. In the example shown, to the left, case modules 302 and 304 are connected by a conductive wire 309, while to the right these modules are connected by a conductive junction 307 (which may also comprise a conduit for providing to module 302 power and ground wires from the battery in module 304). The left and right connections could also be made similarly. Once the case modules 302 and 304 are connected, Icase will flow via Eddy currents through both of case modules 302 and 304 as shown. A lower conductivity gap 303 as before intervenes between conductive regions 305, with antenna wires connected to the regions 305 across the gap. These antenna wires as before will carry Ipower to the capacitor 105 and associated circuitry to allow IMD 300 to be powered or charged as explained earlier.

FIG. 14 shows another example of an improved IMD 320 able to harness Eddy currents to provide IMD power, but which lacks a header connected to the case. IMD 320 is also generally shown in the above-referenced 2017/0151440 Publication, which with the reader is assumed familiar. IMD 320 is generally divided into three sections: an electronics section 322, a connector block section 324, and an electrode wire section 326. Sections 324 and 326 are further comprised in this example of left and right connector blocks 325*a* and 325*b*, each coupled to its own electrode wire cable 327*a* and 327*b*, which cables can be flexible. The proximal ends of leads 18 (FIG. 1A) can couple openings in the connector blocks 325*a* and 325*b*. Electrode wires in the electrode wire cables 327*a* and 327*b* connect to contacts in the connector blocks, and connect to stimulation circuitry inside the electronics section 322.

Electronics section 320 includes a case 330 which in this example is generally cylindrical, and having a major planar surface facing outwardly of the patient when implanted. This surface includes a higher conductivity region 335 which surrounds a lower conductivity region 336 which includes a gap 333. These regions 335 and 336 can be formed in any of the ways previously mentioned, and can be formed of different combinations of materials also previously mentioned. Antenna wires connect to the higher conductivity region 335 across the gap 333, and are connected to the capacitor 105 and other aspects of the power reception circuitry 101 as before to allow Eddy current formed in region 335 to provide power for the IMD 320. IMD 320 can include an overmold 350 that overmolds one or all of the electronics 322, connector block 324, and electrode wire 326 sections. This overmold 350 can include an opening (e.g., 264*a*, FIG. 12B) for a case electrode, although this isn't shown.

The various disclosed examples of IMDs capable of receiving power using Eddy currents and without wire-wound coils can operate using a range of frequencies, and as such the AC magnetic field 55 produced by the external charger can comprise a range of frequencies. The frequency used to provide power to the various disclosed IMDs may be higher than is traditionally used in IMDs using wire-wound coils 30 to pick up the magnetic field 55. For example, while IMDs having traditional wire-wound coils 30 may be tuned to receive magnetic fields 55 having frequencies on the order of 100 kHz, the disclosed examples may be tuned to receive magnetic fields 55 having frequencies on the order of 1 to 10 MHz. In one specific example, ISM band frequencies of 6.78 MHz or 13.56 MHz can be used. The use of higher frequencies to provide power to the disclosed IMDs may be preferred to reduce heating in the case in which the Eddy currents are induced. As one skilled in the art will appreciate, current Icase flows with a skin depth which is inversely proportional with frequency. Higher frequencies will thus decrease the skin depth, which will tend to reduce Icase, but will also reduce heating. One skilled will understand that the IMD can be tuned to resonate at the frequency of the magnetic field 55 by varying the capacitance 105. In one example, for the higher frequencies discussed, capacitor 105 can have a value ranging from 1 to 100 nanoFarads.

As one skilled in the art will appreciate, the foregoing examples show several different means by which an IMD can wirelessly receive power from an external charger to power or charge the IMD using case-induced Eddy currents and without the need for a wire-wound coil. It should be appreciated that these various examples are not exclusive to one another, and thus that techniques used in certain examples can be combined with different examples. All such variations are not expressly shown as it would be burdensome to do so.

Further, while the foregoing examples are shown in the context of an implantable stimulator device, one skilled in the art will appreciate that many differently implantable medical devices can be powered or charged using magnetic induction, and all such implantable devices can therefore benefit from the teachings provided in this disclosure. This is true even for implantable medical devices that may lack a header altogether. Non-implantable or non-medical devices having conductive case portions and able to be powered or charged using magnetic induction can also benefit.

What is claimed is:

1. An implantable medical device (IMD) configured to wirelessly receive power from an electromagnetic field, comprising:
   a case housing control circuitry for the IMD, wherein at least a portion of the case is conductive and comprises a conductive case portion, and wherein a case current is formed in the conductive case portion in response to the electromagnetic field;
   power reception circuitry inside the case;
   a non-conductive header affixed to the case; and
   a first electrical connection and a second electrical connection to divert at least some of the case current as a power current to the power reception circuitry, wherein at least one of the first electrical connection and the second electrical connection comprises an antenna portion in or on the non-conductive header, resulting in at least one antenna portion in or on the non-conductive header,
   wherein the power reception circuitry is configured to use the power current to provide power to the IMD.

2. The IMD of claim 1, further comprising one or more lead connectors in the non-conductive header, a feedthrough between the non-conductive header and the case, and a plurality of electrode feedthrough wires, wherein the electrode feedthrough wires connect to contacts in the one or more lead connectors and pass through the feedthrough inside the case.

3. The IMD of claim 2, wherein at least one of the first electrical connection and the second electrical connection comprises a feedthrough wire connected to the at least one antenna portion that passes through the feedthrough.

4. The IMD of claim 1, wherein the at least one antenna portion is formed of a material of the case.

5. The IMD of claim 1, wherein there is a first antenna portion in or on the non-conductive header comprising the first electrical connection, and a second antenna portion in or on the non-conductive header comprising the second electrical connection.

6. The IMD of claim 5, wherein the first antenna portion comprises a first end and a second end, and wherein the second antenna portion comprises a first end and a second end.

7. The IMD of claim 6, wherein the first electrical connection further comprises a first wire connected to the first end of the first antenna portion, wherein the second end of the first antenna portion is connected to the conductive case portion, wherein the second electrical connection further comprises a second wire connected to the first end of the second antenna portion, wherein the second end of the second antenna portion is connected to the conductive case portion.

8. The IMD of claim 1, wherein there is a single antenna portion in or on the non-conductive header comprising the first electrical connection.

9. The IMD of claim 8, wherein the single antenna portion comprises a first end and a second end, wherein the first electrical connection further comprises a first wire connected to the first end of the single antenna portion, wherein the second end of the single antenna portion is connected to the conductive case portion.

10. The IMD of claim 1, wherein there is a single antenna portion in or on the non-conductive header comprising the first electrical connection and the second electrical connection.

11. The IMD of claim 1, wherein at least one of the first electrical connection and the second electrical connection comprises a wire connected to the conductive case portion.

12. The IMD of claim 1, wherein the power reception circuitry comprises a rectifier configured to convert the power current to a direct current (DC) voltage that is used to provide power to the IMD.

13. The IMD of claim 1, further comprising a battery within the case, wherein the power reception circuitry is configured to use the power current to provide power to the IMD to charge the battery.

14. The IMD of claim 1, wherein the conductive case portion comprises a conductive layer applied to the case.

15. The IMD of claim 1, wherein the case comprises a dielectric material, and wherein the conductive case portion comprises a conductive window.

16. The IMD of claim 1, wherein the power reception circuitry is not coupled to a wire-wound coil configured to receive the electromagnetic field.

* * * * *